(12) United States Patent
Yamamoto et al.

(10) Patent No.: US 12,708,467 B2
(45) Date of Patent: Aug. 18, 2026

(54) OPERATION DEVICE, ROBOTIC SURGICAL SYSTEM AND OPERATION-DEVICE CONTROL METHOD

(71) Applicant: KAWASAKI JUKOGYO KABUSHIKI KAISHA, Kobe (JP)

(72) Inventors: Daisuke Yamamoto, Kobe (JP); Takeshi Kurihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 241 days.

(21) Appl. No.: 18/473,331

(22) Filed: Sep. 25, 2023

(65) Prior Publication Data

US 2024/0099793 A1 Mar. 28, 2024

(30) Foreign Application Priority Data

Sep. 27, 2022 (JP) ................................ 2022-154131

(51) Int. Cl.
*A61B 34/37* (2016.01)
*A61B 34/00* (2016.01)
*A61B 34/30* (2016.01)

(52) U.S. Cl.
CPC .............. *A61B 34/37* (2016.02); *A61B 34/70* (2016.02); *A61B 2034/305* (2016.02)

(58) Field of Classification Search
CPC ... A61B 34/37; A61B 34/70; A61B 2034/305; A61B 34/77; A61B 34/74
See application file for complete search history.

(56) References Cited

U.S. PATENT DOCUMENTS

| | | | | |
|---|---|---|---|---|
| 8,989,902 | B1 * | 3/2015 | Crawford | A61B 34/30 700/257 |
| 2002/0120363 | A1 * | 8/2002 | Salisbury | B25J 9/1643 700/254 |
| 2007/0158385 | A1 * | 7/2007 | Hueil | A61B 17/07207 227/175.1 |
| 2017/0367773 | A1 * | 12/2017 | Kottenstette | A61B 34/30 |
| 2019/0089273 | A1 * | 3/2019 | Kirby | H02P 3/24 |
| 2020/0384643 | A1 * | 12/2020 | Hariri | B25J 9/1664 |
| 2021/0038336 | A1 * | 2/2021 | Ogata | A61B 34/76 |
| 2022/0110705 | A1 * | 4/2022 | Hourtash | A61B 34/30 |

FOREIGN PATENT DOCUMENTS

| | | | | |
|---|---|---|---|---|
| JP | 2021-023706 A | | 2/2021 | |
| WO | WO-2022115877 A1 | * | 6/2022 | A61B 90/37 |

* cited by examiner

*Primary Examiner* — Ramon A. Mercado
*Assistant Examiner* — John Martin O'Malley
(74) *Attorney, Agent, or Firm* — METROLEX IP LAW GROUP, PLLC; Robert L. Scott, Esq.

(57) ABSTRACT

An operation device according to this disclosure includes a control device configures to execute following control that keep an angle formed by a second link part and a first link part at a predetermined angle, and a rotation amount of a following link part about a following rotation axis in a case in which an absolute value of a moving speed of a wrist part is smaller than a predetermined threshold(s) is smaller than in a case in which the absolute value is not smaller than the predetermined threshold(s).

14 Claims, 22 Drawing Sheets

500
30
32 33
100
40
20
32
33
32
50
33
50a
50b
31
60
50d
10
1
2
50c
33
3
1
330
320
310
P
200
150
140
220
141
160
161
400
210
110L
130
240
300
230
110
110R
120
340

30
10
BRK
EN4
SM4
BRK
EN4
SM4
EN5
SM5
BRK
EN6
SM6
SC4
SC4
SC5
SC6
POSITIONER CONTROLLER
330

341
AG26(0)
AG26
341a
−
+
REDUCTION RATIO CORRECTOR
341b
PRIMARY FILTER
341c
DEAD BAND PART
341d
f1
341e
f2
341f
MOVING AVERAGE PART
341g
Xe
COEFFI-CIENT MULTIPLIER
341h
AG26
v1

FIG.29

OPERATION DEVICE, ROBOTIC SURGICAL SYSTEM AND OPERATION-DEVICE CONTROL METHOD

CROSS-REFERENCE TO RELATED APPLICATION

The priority application number JP2022-154131, an operation device, a robotic surgical system and an operation-device control method, Sep. 27, 2022, Daisuke YAMAMOTO, and Takeshi KURIHARA, upon which this patent application is based, are hereby incorporated by reference.

BACKGROUND OF THE INVENTION

Field of the Invention

The present disclosure relates to an operation device, a robotic surgical system, and an operation-device control method.

Description of the Background Art

Conventionally, a robotic surgical system including a robot arm to which a surgical instrument is attached is known. United States patent application publication No. US2002/0120363 discloses a robot operation system including manipulator arms and a master device configured to control the manipulator arm. The master device includes a pair of wrist parts configured to be operated by operator's right and left hands. The wrist part includes a plurality of link parts, and a handle configured to be grasped by operator's fingers. An arm, the plurality of link parts and a handle are connected to each other in this order by joints. The joint includes an electric motor. In the system disclosed in the United States patent application publication No. US2002/0120363, the other link parts rotate following the rotation of the one link part to form right angles between rotation axes of the plurality of link parts. The other link parts are rotated by their electric motors in the joints.

In a configuration disclosed in the United States patent application publication No. US2002/0120363, the other link parts rotate to follow the rotation of the one link part. However, in the configuration disclosed in the United States patent application publication No. US2002/0120363, in a case in which a rotation speed of one link is relatively slow, it is conceivable that the other link parts cannot rotate to follow the rotation of the one link part because torques of the electric motors of joints rotating the other link parts are small, and relatively large friction is produced in the joints. When the rotation speed of one link then gradually increases, and the torques of the electric motors rotating the joints increase, the other link parts will start to rapidly rotate. In this case, because the other link parts that cannot rotate to follow the rotation of the one link part and are stationary start to rapidly rotate, it is conceivable that a surgical instrument cannot smoothly move to follow an operation on the master device by an operator.

SUMMARY OF THE INVENTION

The present disclosure provides an operation unit, a robotic surgical system, and an operation-device control method capable of smoothly moving a surgical instrument to follow an operation on an operation unit by an operator even when a moving speed of a wrist part is relatively slow.

An operation device according to a first aspect of the present disclosure includes an operation unit configured to accept an operation on a surgical instrument attached to a distal end of a robot arm; and a controller, wherein the operation unit includes an arm part and a wrist part, the wrist part includes a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the controller is configured to execute following control in which the following link part is rotated about the following rotation axis based on a rotational position of the second link part by the driver to keep an angle formed by the second link part and the first link part at a predetermined angle, and a rotation amount of the following link part about the following rotation axis in the following control in a case in which an absolute value of a moving speed of the wrist part by the operation of the operator is smaller than a predetermined threshold(s) is smaller than in a case in which the absolute value is not smaller than the predetermined threshold(s). In this specification, the term that a rotation amount is small or smaller is used in a broad sense to include that the rotation amount is zero.

In the operation device according to the first aspect of the present disclosure, as discussed above, a rotation amount of the following link part about the following rotation axis in the following control in a case in which an absolute value of a moving speed of the wrist part by the operation of the operator is smaller than a predetermined threshold(s) is smaller than in a case in which the absolute value is not smaller than the predetermined threshold(s). Accordingly, when an absolute value of a moving speed of the wrist part by the operation of the operator is smaller than a predetermined threshold(s), for example, when the absolute value is relatively slow, a rotation amount of the following link part about the following rotation axis is small. As a result, even in a case in which a moving speed of the wrist part by operator's operation gradually increases, even when the following link part starts to rotate, the rotation amount of the following link part is small. In other words, it is possible to prevent that the following link part that cannot rotate to follow a rotation of the second link part and is stationary starts to rapidly rotate. Therefore, a surgical instrument can be smoothly moved to follow an operation on an operation unit by an operator even when a moving speed of a wrist part is relatively slow.

A robotic surgical system according to a second aspect of the present disclosure includes a surgical device including a robot arm including a distal end to which a surgical instrument is attached; an operation device including an operation unit configured to accept an operation on the surgical instrument; and a controller, the operation unit includes an arm part and a wrist part, the wrist part includes a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the controller is configured to execute following control in which the following link part is rotated about the following rotation axis based on a rotational position of the second link part by the driver to keep an angle formed by the second link part and the first link part at a predetermined angle, and a rotation amount of the following link part about the following rotation axis in the following control in a case in which an absolute value of a moving speed of the wrist part by the operation of the operator is smaller than a predetermined threshold(s) is smaller than in a case in which the absolute value is not smaller than the predetermined threshold(s).

In the robotic surgical system according to the second aspect of the present disclosure, as discussed above, a rotation amount of the following link part about the following rotation axis in the following control in a case in which an absolute value of a moving speed of the wrist part by the operation of the operator is smaller than a predetermined threshold(s) is smaller than in a case in which the absolute value is not smaller than the predetermined threshold(s). Accordingly, when an absolute value of a moving speed of the wrist part by the operation of the operator is smaller than a predetermined threshold(s), for example, when the absolute value is relatively slow, a rotation amount of the following link part about the following rotation axis is small. As a result, even in a case in which a moving speed of the wrist part by operator's operation gradually increases, when the following link part starts to rotate, the rotation amount of the following link part is small. In other words, it is possible to prevent that the following link part that cannot rotate to follow a rotation of the second link part and is stationary starts to rapidly rotate. Therefore, it is possible to provide a robotic surgical system capable of smoothly moving a surgical instrument to follow an operation on an operation unit by an operator even when a moving speed of a wrist part is relatively slow.

An operation-device control method according to a third aspect of the present disclosure is a method of an operation device including an operation unit configured to accept an operation on a surgical instrument attached to a distal end of a robot arm, and a controller, the operation unit including an arm part and a wrist part, the wrist part including a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the method including acquiring a rotational position of the second link part; and executing following control in which the following link part is rotated about the following rotation axis based on the rotational position of the second link part by the driver to keep an angle formed by the second link part and the first link part at a predetermined angle, wherein a rotation amount of the following link part about the following rotation axis in the following control in a case in which an absolute value of a moving speed of the wrist part by the operation for operating the surgical instrument is smaller than a predetermined threshold(s) is smaller than in a case in which the absolute value is not smaller than the predetermined threshold(s).

In the operation-device control method according to the third aspect of the present disclosure, as discussed above, a rotation amount of the following link part about the following rotation axis in the following control in a case in which an absolute value of a moving speed of the wrist part by the operation of the operator is smaller than a predetermined threshold(s) is smaller than in a case in which the absolute value is not smaller than the predetermined threshold(s). Accordingly, when an absolute value of a moving speed of the wrist part by the operation of the operator is smaller than a predetermined threshold(s), for example, when the absolute value is relatively slow, a rotation amount of the following link part about the following rotation axis is small. As a result, even in a case in which a moving speed of the wrist part by operator's operation gradually increases, when the following link part starts to rotate, the rotation amount of the following link part is small. In other words, it is possible to prevent that the following link part that cannot rotate to follow a rotation of the second link part and is stationary starts to rapidly rotate. Therefore, it is possible to provide an operation-device control method capable of smoothly moving a surgical instrument to follow an operation on an operation unit by an operator even when a moving speed of a wrist part is relatively slow.

According to the disclosure, a surgical instrument can be smoothly moved to follow an operation on an operation unit by an operator even when a moving speed of a wrist part is relatively slow.

BRIEF DESCRIPTION OF THE DRAWINGS

FIG. 29 is a flowchart illustrating a control-flow of an operation device according to the one embodiment.

Figure 1:
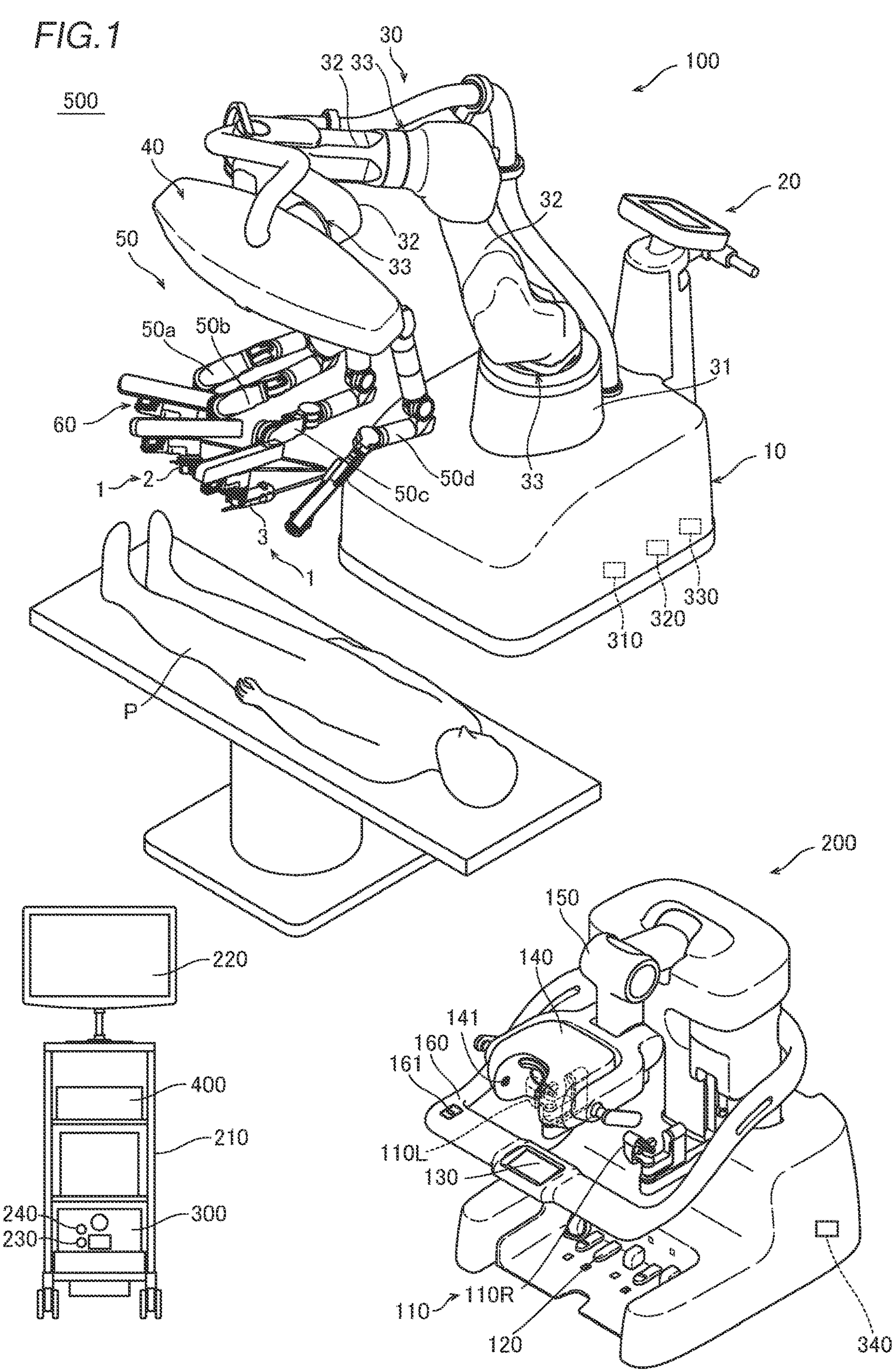
FIG. 1 is a block diagram showing a configuration of a robotic surgical system according to one embodiment.

DESCRIPTION OF THE PREFERRED EMBODIMENT (Configuration of Robotic Surgical System)

The following description describes a configuration of a robotic surgical system 500 according to this embodiment. The robotic surgical system 500 includes a surgical robot 100, a remote control apparatus 200, a vision unit 300 and an image processing unit 400. The surgical robot 100 and the remote control apparatus 200 are an example of a surgical apparatus and an example of an operation device, respectively.

Figure 4:
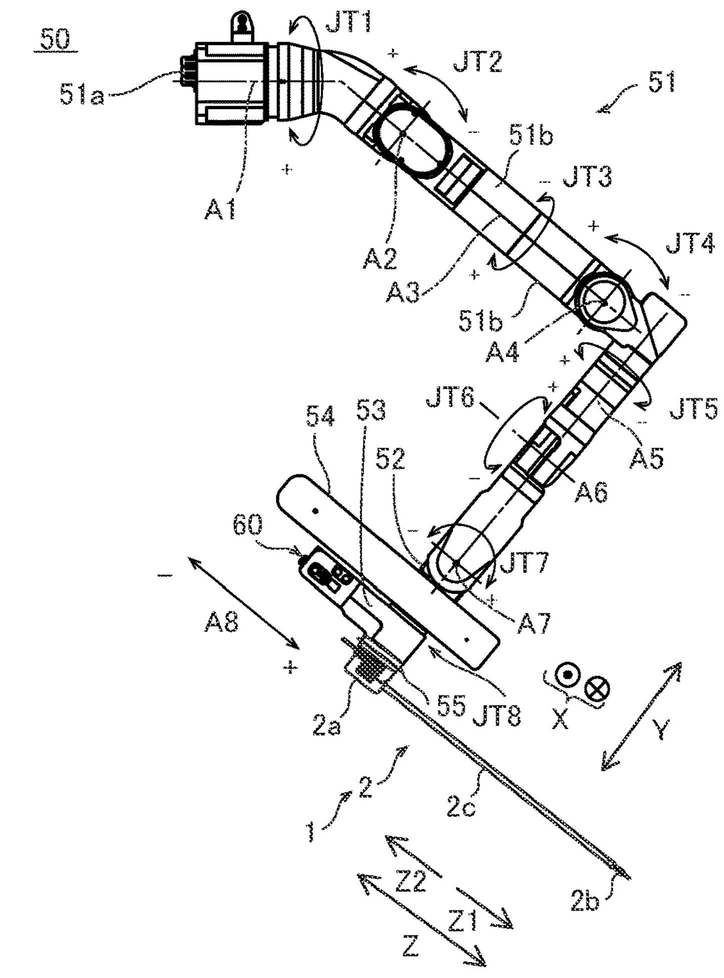
FIG. 4 is a block diagram showing a configuration of a robot arm according to the one embodiment.

In this specification, a longitudinal direction of a surgical instrument 1 is defined as a Z direction as shown in FIG. 4. A distal end side of the surgical instrument 1 is defined as a Z1 side, and a proximal end side of the surgical instrument 1 is defined as a Z2 side. A direction orthogonal to the Z direction is defined as an X direction. A direction orthogonal to the Z direction and the X direction is defined as a Y direction.

Figure 3:
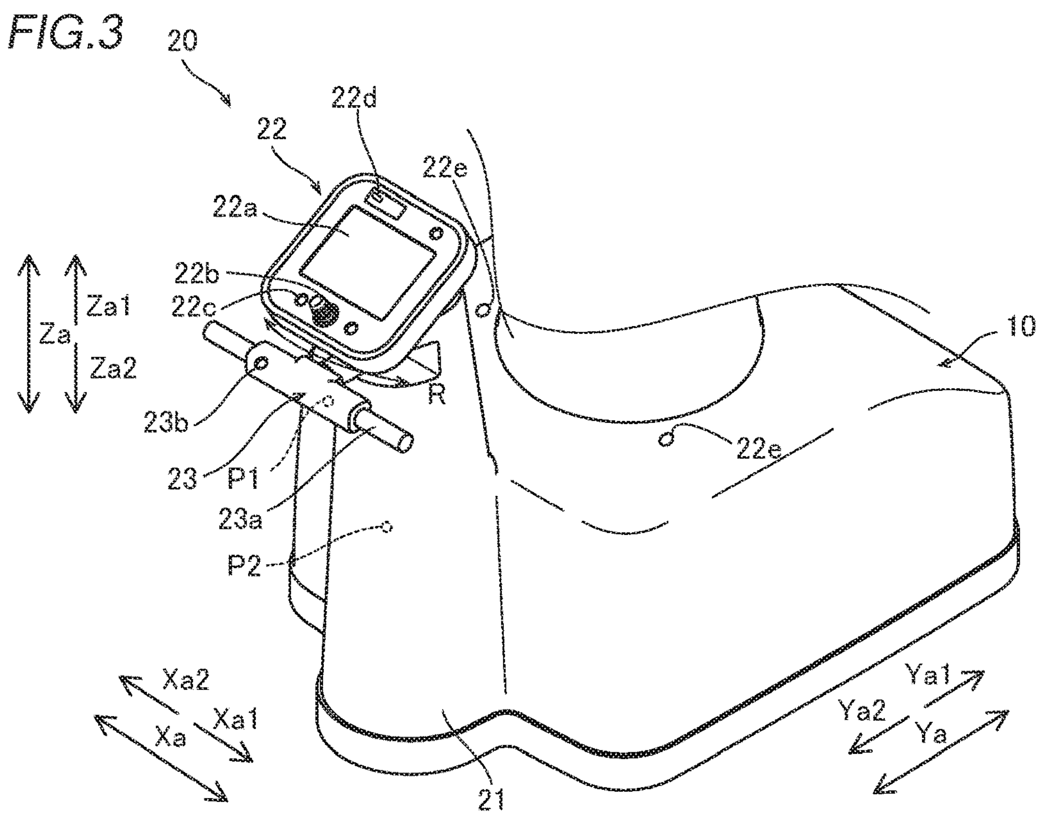
FIG. 3 is a diagram showing a configuration of the medical cart according to the one embodiment.

In this specification, a leftward/rightward direction from the viewpoint of an operator who operates a display 22*a* of an input 22 is defined as an Xa direction as shown in FIG. 3. A rightward direction is defined as an Xa1 direction, and a leftward direction is defined as an Xa2 direction. A frontward/rearward direction from the viewpoint of the operator who operates the display 22*a* of the input 22 is defined as a Ya direction. A frontward direction is defined as an Ya1 direction, and a rearward direction is defined as an Ya2 direction. A direction orthogonal to a floor on which the surgical robot 100 is arranged is defined as a Za direction. An upward direction is defined as a Za1 direction, and a downward direction is defined as a Za2 direction.

In this specification, a direction orthogonal to a floor on which the remote control apparatus 200 is placed is defined as a Zb direction, the frontward/rearward direction of the operator who operates the operation unit 110, which is orthogonal to the Zb direction, is defined a Yb direction, and a direction orthogonal to the Zb direction and the Yb direction is defined as an Xb direction. In the Zb directions, an upward direction is defined as a Zb1 direction, and a downward direction is defined as a Zb2 direction. In the Yb directions, one is defined as an Yb1 direction, and another is defined as an Yb2 direction. In the Xb directions, one is defined as an Xb1 direction, and another is defined as an Xb2 direction. Axes corresponding to the Xb, Yb and Zb directions are occasionally referred to as Xb, Yb and Zb axes, respectively.

As shown in FIG. 1, the surgical robot 100 is arranged in an operating room. The remote control apparatus 200 is located remote from the surgical robot 100. Also, the remote control apparatus 200 is configured to receive instructions as to the surgical instruments 1. Specifically, an operator, such as a doctor, can provide the remote control apparatus 200 with an instruction to instruct a desired motion of the surgical robot 100. The remote control apparatus 200 transmits the provided instruction to the surgical robot 100. The surgical robot 100 is configured to perform the motion in accordance with the instruction received. The surgical robot 100 is arranged in the operating room, which is a sterile field.

(Configuration of Surgical Robot)

As shown in FIG. 1, the surgical robot 100 includes a medical cart 10, a cart positioner operation unit 20, a positioner 30, an arm base 40, a plurality of robot arms 50 and arm operation units 60 provided in the robot arms 50.

As shown in FIG. 3, the cart positioner operation unit 20 is arranged in a rear part of the medical cart 10 and supported by a cart positioner operation support 21, and the medical cart 10 or the positioner 30 can be moved in accordance with a manual operation on the cart positioner operation unit 20. The cart positioner operation unit 20 includes the input 22 and an operating handle 23. The input 22 is configured to accept instructions to move or change orientations of the positioner 30, the arm base 40 and the plurality of robot arms 50 to prepare a surgical operation mainly before the operation is carried out. The cart positioner operation unit 20 includes the operating handle 23, a stabilizer 24 and an electric cylinder 25 shown in FIG. 17.

Figure 2:
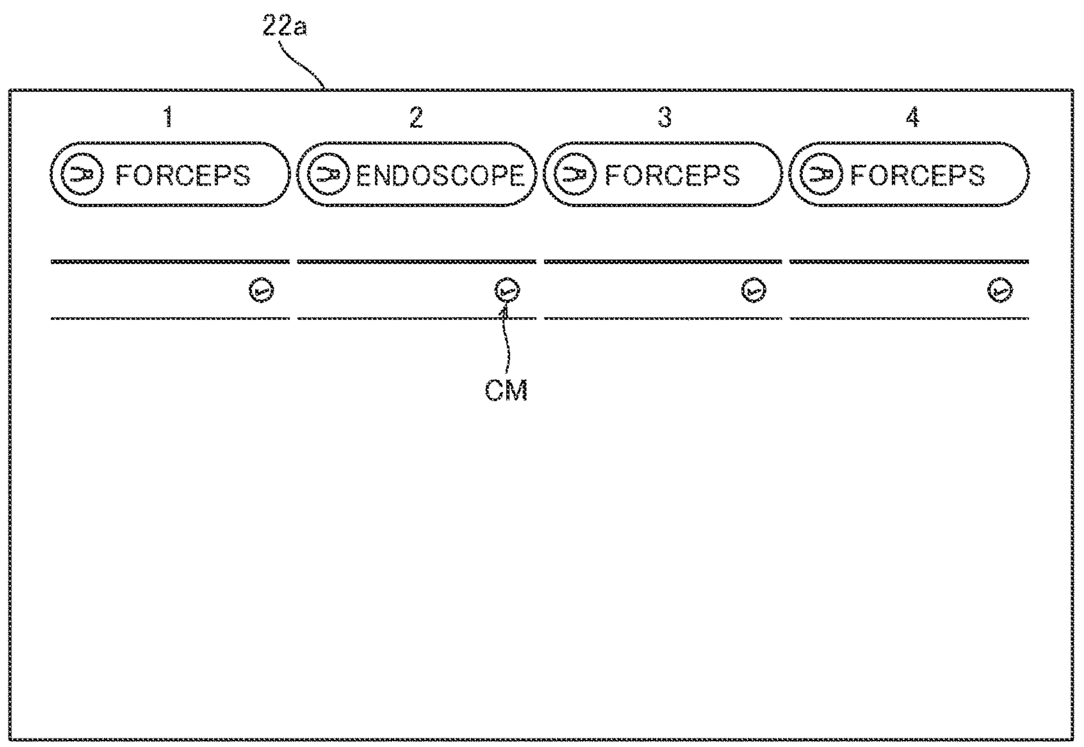
FIG. 2 is a diagram showing a display of a medical cart according to the one embodiment.

As shown in FIG. 3, the input 22 of the cart positioner operation unit 20 includes the display 22*a*, a joystick 22*b*, an enable switch 22*c*, an error reset button 22*d* and speakers 22*e*. For example, the display 22*a* is a liquid crystal panel. As shown in FIG. 2, the display 22*a* indicates numbers corresponding to the plurality of robot arms 50. Also, the display 22*a* indicates types of surgical instruments 1 attached to the plurality of robot arms 50. The display 22*a* indicates checkmarks CM representing that their pivot positions PP (discussed later) have been set.

As shown in FIG. 3, the joystick 22*b* is arranged in proximity to the display 22*a* of the input 22 of the cart positioner operation unit 20. When an operation mode displayed on the display 22*a* is selected, the positioner 30 can be three-dimensionally moved by operating the joystick 22*b*.

The enable switch 22*c* is arranged in proximity to the joystick 22*b* of the cart positioner operation unit 20. The enable switch 22*c* is configured to enable or disable movement of the positioner 30. When the enable switch 22*c* is pressed so that movement of the positioner 30 is enabled, the positioner 30 can be moved in accordance with a manual operation on the joystick 22*b*.

The error reset button 22*d* is configured to reset an error of the robotic surgical system 500. An exemplary error is an error of abnormal deviation. The speakers 22*e* are a a pair of speakers. The pair of speakers 22*e* are arranged at a position in the medical cart 10 in proximity to the positioner 30.

Also, the operating handle 23 is arranged in proximity to the display 22*a* of the cart positioner operation unit 20. The operating handle 23 includes a throttle grip 23*a* that is configured to be gripped and twisted by an operator such as nurse, engineer, etc. to control movement of the medical cart 10. Specifically, the operating handle 23 is arranged under the input 22. The medical cart 10 can move forward when the throttle grip 23*a* is twisted from a near side toward a far side. The medical cart 10 can move backward when the throttle grip 23*a* is twisted from the far side toward the near side. A speed of the medical cart 10 can be changed in accordance with a twisting amount of the throttle grip 23*a*. In addition, the operating handle 23 is configured to swing leftward and rightward as shown by an R direction, and to rotate the medical cart 10 depending on the swinging operation on the operating handle 23.

Also, the operating handle 23 of the cart positioner operation unit 20 includes an enable switch 23*b* configured to enable or disable movement of the medical cart 10. When the enable switch 23*b* is pressed so that movement of the medical cart 10 is enabled, the medical cart 10 can be moved in accordance with a manual operation on the throttle grip 23*a* of the operating handle 23.

For example, as shown in FIG. 1, the positioner 30 is constructed of a 7-axis multi-joint robot. The positioner 30 is arranged on the medical cart 10. The positioner 30 is configured to adjust a position of the arm base 40. The positioner 30 can three-dimensionally move the position of the arm base 40.

The positioner 30 includes a base 31, and a plurality of links 32 coupled to the base 31. The links 32 are coupled to each other by joints 33.

The arm base 40 is attached to a distal end of the positioner 30. The proximal ends of the plurality of robot arms 50 are attached to the arm base 40. The plurality of robot arms 50 are foldable into a storage posture. The arm base 40 and the plurality of robot arms 50 covered by sterile drapes when used. The robot arm 50 is configured to support surgical instruments 1.

Figure 17:
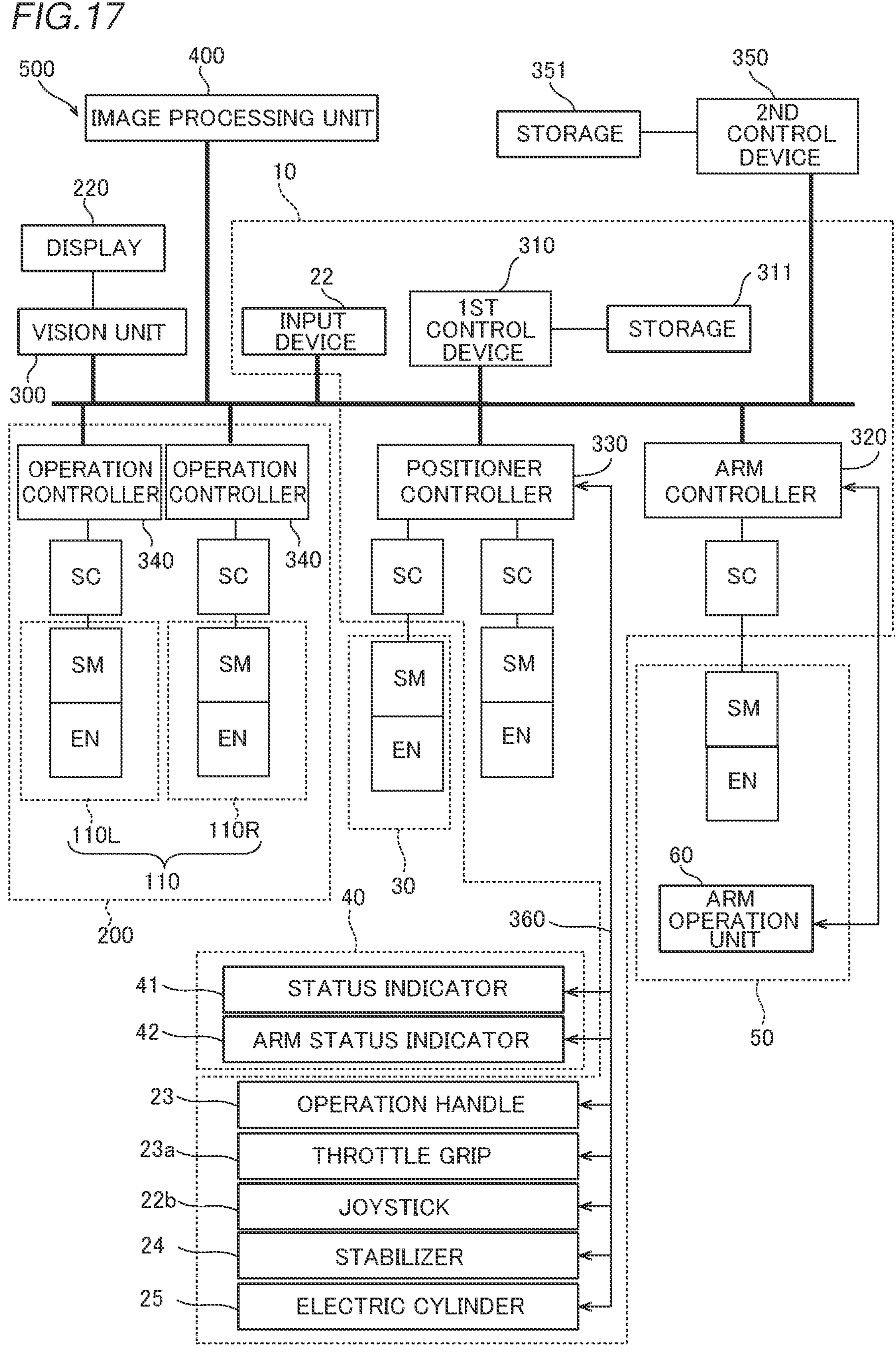
FIG. 17 is a control block diagram of a surgical robot according to the one embodiment.

A status indicator 41 and an arm status indicator 42 shown in FIG. 17 are provided in the arm base 40. The status indicator 41 is configured to indicate a status of robotic surgical system 500. The arm status indicator 42 is configured to indicate states of robot arms 50.

Two or more robot arms 50 are provided as a plurality of robot arms. Specifically, four robot arms 50*a*, 50*b*, 50*c* and 50*d* are provided. The robot arms 50*a*, 50*b*, 50*c* and 50*d* have a similar configuration to each other.

As shown in FIG. 4, each robot arm 50 includes an arm 51, a first link part 52, a second link part 53, and a translation mechanism 54. The robot arm 50 includes joints JT1, JT2, JT3, JT4, JT5, JT6, JT7 and JT8. The joints JT1, JT2, JT3, JT4, JT5, JT6 and JT7 have A1, A2, A3, A4, A5, A6 and A7 axes as their rotation axes. JT8 has an A8 axis as its linear-motion axis. The axes from A1 to A7 are rotation axes of JT1 to JT7 of the arm 51. The A7 axis is a rotational axis of the first link part 52. The A8 axis is a linear-motion axis along which the second link part 53 is moved relative to the first link part 52 in the Z direction by the translation mechanism 54. The arm 51 includes a base 51*a* and a link part 51*b*.

The arm 51 is constructed of a 7-axis multi-joint robot arm. The first link part 52 is arranged in a distal end of arm 51. The arm operation unit 60 discussed later is attached to the second link part 53. The translation mechanism 54 is arranged between the first link part 52 and the second link part 53. The second link part 53 includes a holder 55 configured to hold the surgical instrument 1. The translation mechanism 54 is configured to translationally move the holder 55 to which the surgical instrument 1 is attached between a first position and a second position. The first position is a position of a Z2-direction side end of a moving range of the holder 55 moved by the translation mechanism 54 along the A8 axis. The second position is a position of a Z1-direction side end of the moving range of the holder 55 moved by the translation mechanism 54 along the A8 axis.

Figure 9:
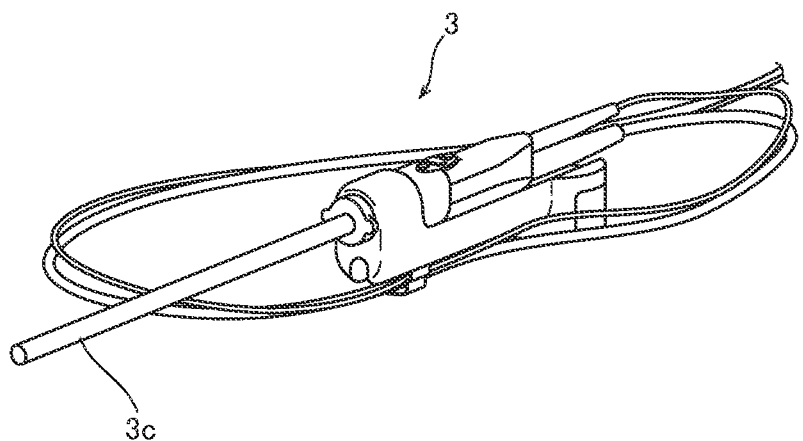
FIG. 9 is a diagram showing an endoscope.
Figure 10:
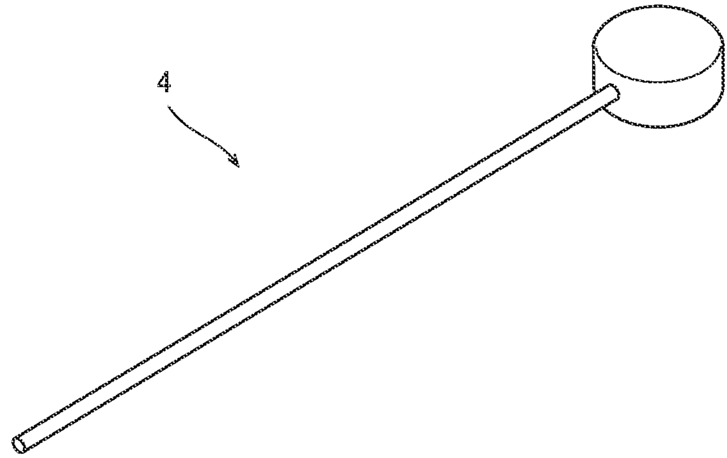
FIG. 10 is a diagram showing a pivot-position setting tool.

Surgical instruments 1 can be attached to the distal ends of the plurality of robot arms 50. The surgical instruments 1 include, for example, replaceable instruments 2, an endoscope 3 (see FIG. 9) configured to capture images of a part to be operated, a pivot-position setting tool 4 (see FIG. 10) to set a pivot position PP described below, etc. The instrument 2 includes a driven unit 2*a*, a forceps 2*b* and a shaft 2*c*.

As shown in FIG. 1, an endoscope 3 is attached to the distal end of one, e.g., the robot arm 50*c* of the robot arms 50, and the instruments 2 are attached to the distal ends of the others, e.g., the robot arms 50*a*, 50*b* and 50*d*. The endoscope 3 is preferably attached to one of two robot arms 50*b* and 50*c*, which are located in a central part, of the four robot arms 50 arranged adjacent to each other.

(Configuration of Instrument)

Figure 5:
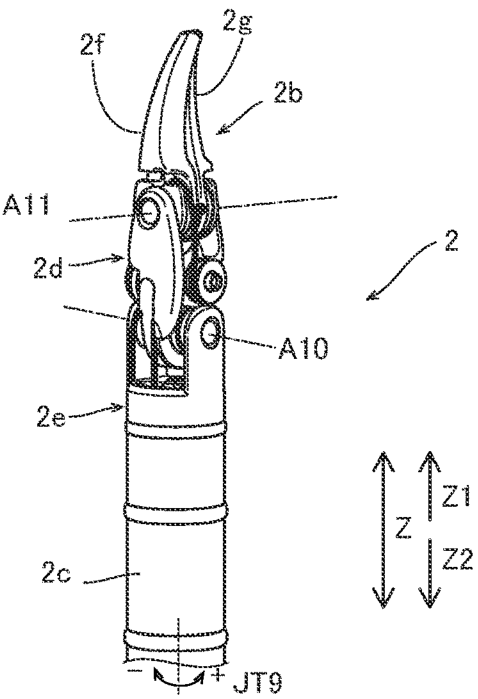
FIG. 5 is a diagram showing a forceps.

For example, as shown in FIG. 5, a forceps 2*b* is attached to the distal end of the instrument 2. Tools that include a joint and can be attached to the distal end of the instrument 2 can include scissors, a grasper, a needle holder, a microdissector, a staple applier, a tucker, a vacuum cleaning tool, a snare wire, a clip applier, etc., other than the forceps 2*b*. Tools that do not include any joint and can be attached to the distal end of the instrument 2 can include a cutting blade, a cautery probe, a cleaner, a catheter, a vacuum orifice, etc.

The forceps 2*b* includes a first support 2*d* and a second support 2*e*. The first support 2*d* is configured to rotatably support a proximal end side of jaws 2*g* and 2*f* about a A11 axis. The second support 2*e* is rotatably configured to support a proximal end side of the first support 2*d* about a A10 axis. The shaft 2*c* can rotate about a A9 axis. The jaws 2*g* and 2*f* can rotate about the A11 axis to open and close.

(Configuration of Arm Operation Unit)

Figure 6:
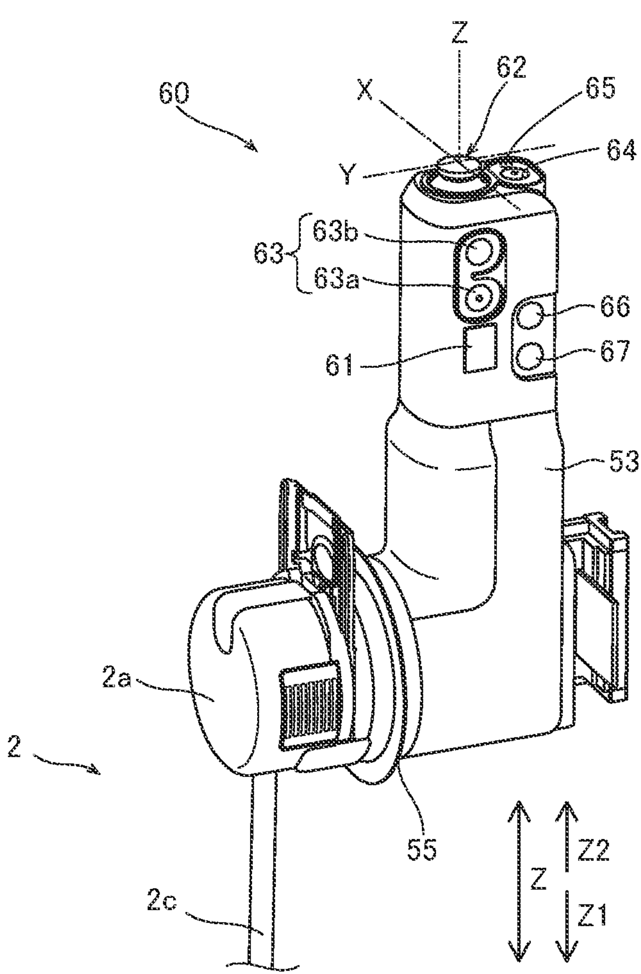
FIG. 6 is a block diagram showing a configuration of an arm operation unit according to the one embodiment.

As shown in FIG. 6, the arm operation unit 60 is mounted to the robot arm 50, and is configured to operate the robot arm 50. Specifically, the arm operation unit 60 is mounted to the second link part 53.

The arm operation unit 60 include an enable switch 61, a joystick 62, linear switches 63, a mode switching button 64, a mode indicator 65, a pivot button 66, and an adjustment button 67.

The enable switch 61 is configured to enable or disable movement of the robot arm 50 by means of the joystick 62 and the linear switches 63 when pressed. Movement of the surgical instrument 1 by the robot arm 50 is enabled when the enable switch 61 is pressed while the arm operation unit 60 is grasped by an operator such as nurse, assistant, etc.

The joystick 62 is an operation tool configured to control movement of the surgical instrument 1 by the robot arm 50. The joystick 62 is an operation tool configured to control a moving direction and a moving speed of the robot arm 50. The robot arm 50 can be moved in accordance with a tilting direction and a tilting angle of the joystick 62.

The linear switches 63 are a switch for moving the surgical instrument 1 in the Z direction, which is a longitudinal direction of the instrument 1. The linear switches 63 includes a linear switch 63*a* for moving the surgical instrument 1 in a direction in which the surgical instrument 1 is inserted into a patient P, and a linear switch 63*b* for moving the surgical instrument 1 in a direction in which the surgical instrument 1 is moved away from the patient P. The linear switch 63*a* and the linear switch 63*b* are constructed of a press-button switch.

Figure 7:
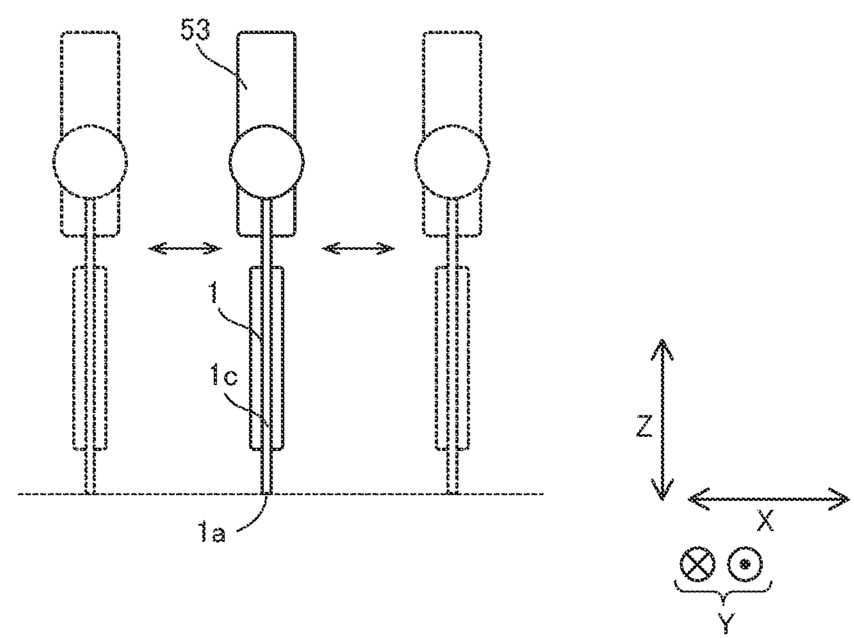
FIG. 7 is a diagram illustrating translational movement of the robot arm.
Figure 8:
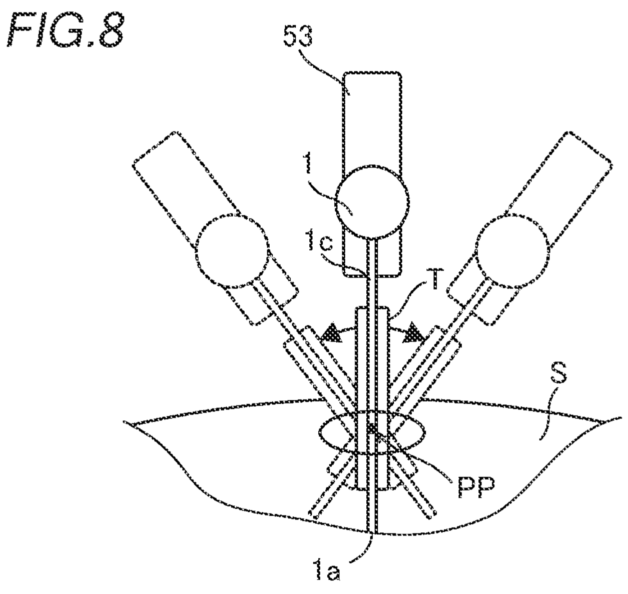
FIG. 8 is a diagram illustrating rotational movement of the robot arm.

The mode switching button 64 is a press-button switch for switching between a translation mode in which the surgical instrument 1 is translationally moved, and a rotation mode in which the surgical instrument 1 is rotated. As shown in FIG. 7, in the translation mode in which the robot arm 50 is translationally moved, the robot arm 50 can be moved so that the distal end 1*a* of the surgical instrument 1 can be moved in an X-Y plane. As shown in FIG. 8, in the rotation mode in which the robot arm 50 is rotated, in a case in which any pivot position PP is not stored in the storage 351, the robot arm 50 can be moved so that the forceps 2*b* can be rotated about a center of the forceps 2*b* of the instrument 2 as the surgical instrument 1 on the A11 axis or the distal end of forceps 2*b* as a rotation axis, and in a case in which a pivot position PP is stored in the storage 351, the robot arm 50 can be moved so that the forceps 2*b* can be rotated about the pivot position PP as a rotation axis. In this case, the surgical instrument 1 is rotated with the shaft 1*c* of the surgical instrument 1 being inserted into a trocar T. The mode switching button 64 is arranged on a surface on a Z-direction side of the arm operation unit 60.

The mode indicator 65 is configured to indicate which mode is selected. The mode indicator 65 is configured to light on to indicate the rotation mode, and to light off indicate the translation mode. The mode indicator 65 also serves as a pivot position indicator to indicate that the pivot position PP is set. The mode indicator 65 is arranged on the surface on the Z-direction side of the arm operation unit 60.

The pivot button 66 is a press-button switch configured to set the pivot position PP, which corresponds to the rotation axis of the surgical instrument 1 attached to the robot arm 50.

The adjustment button 67 is a button configured to optimize a position of the robot arm 50. After the pivot position PP is set with respect to the robot arm 50 to which the endoscope 3 is attached, when the adjustment button 67 is pressed positions of the other robot arms 50 and the arm base 40 is optimized. The adjustment button 67 is a button different from the enable switch 61.

(Remote Control Apparatus)

For example, as shown in FIG. 1, the remote control apparatus 200 is arranged in an operating room or outside the operating room. The remote control apparatus 200 includes operation units 110, foot pedals 120, a touch panel 130, a monitor 140, a support arm 150, a support bar 160, and an error reset button 161. The operation units 110 serves as a handle for operation that is configured to receive instructions from an operator such as doctor.

(Operation Unit)

Figure 11:
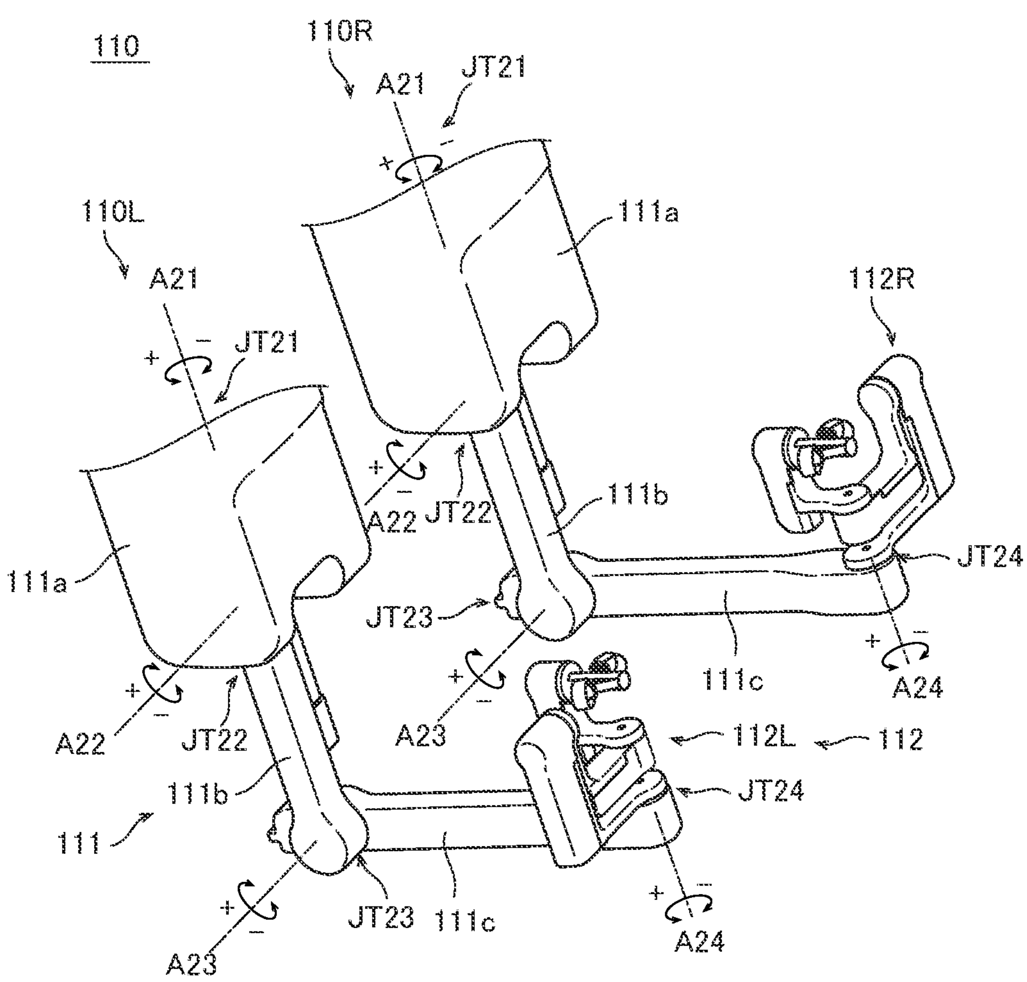
FIG. 11 is a diagram showing operation units according to the one embodiment.

As shown in FIG. 11, the operation units 110 are handle configured to manipulate the surgical instrument 1. Also, the operation units 110 are configured to receive instructions as to the surgical instruments 1. The operation units 110 include an operation unit 110L that is arranged on a left side from viewpoint of an operator such as doctor and is configured to be manually operated by operator's left hand, and an operation unit 110R that is arranged on a right side from viewpoint of the operator such as doctor and is configured to be manually operated by operator's right hand. The operation units 110 include arm parts 111 and wrist parts 112. The operation unit 110R includes an arm part 111R and a wrist part 112R. The operation unit 110L includes an arm part 111L and a wrist part 112L.

Figure 12:
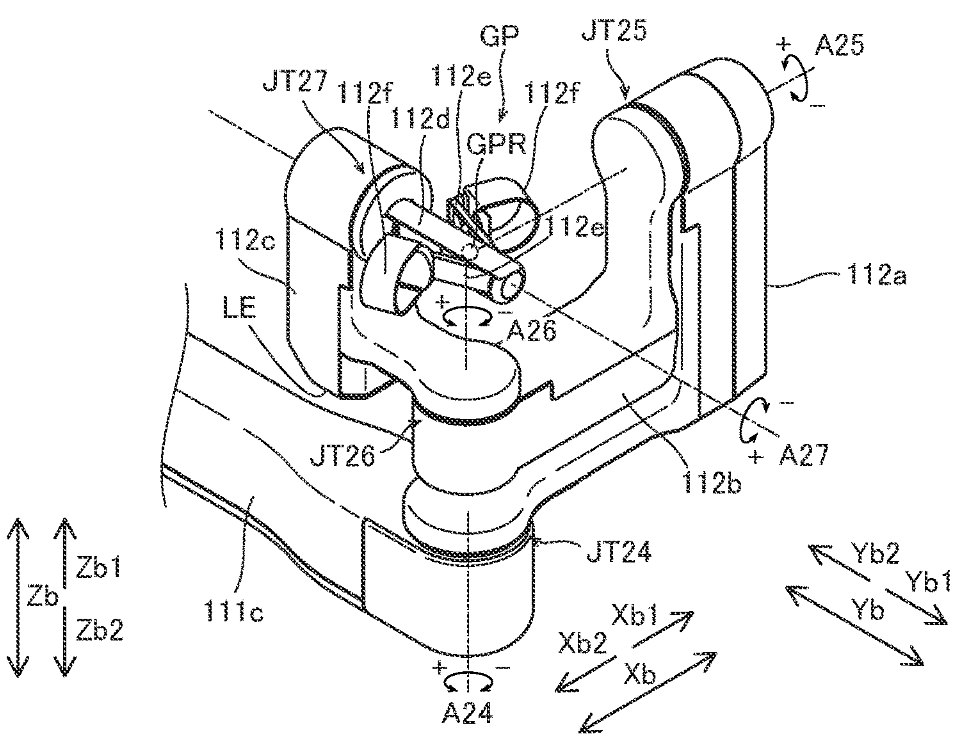
FIG. 12 is a diagram showing a right-hand side wrist part according to the one embodiment.
Figure 13:
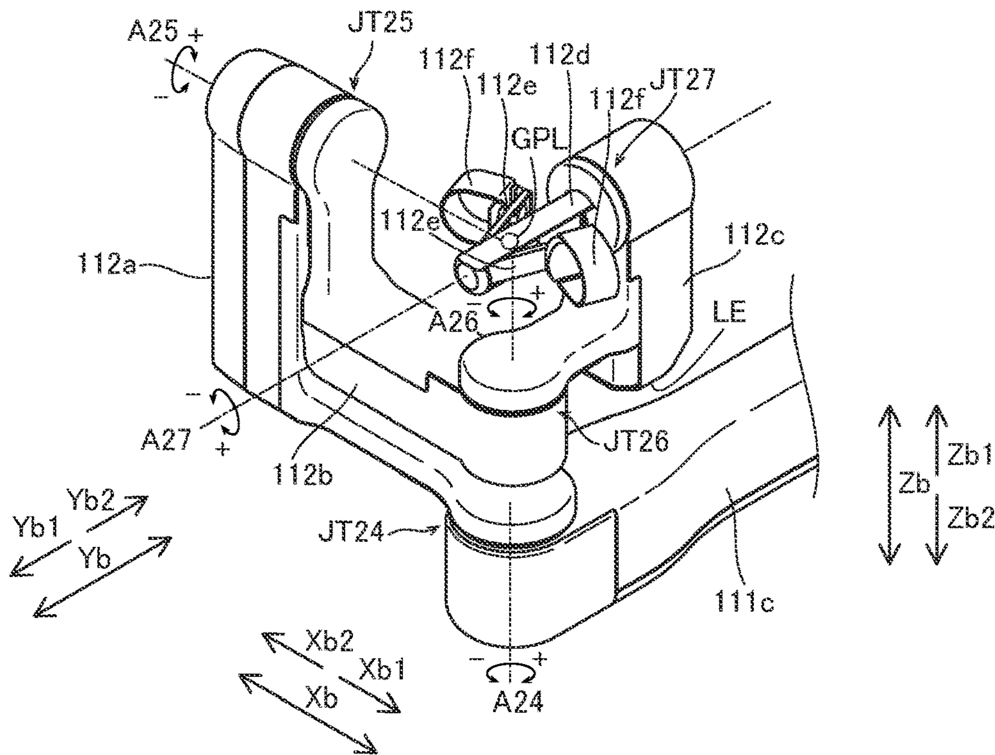
FIG. 13 is a diagram showing a left-hand side wrist part according to the one embodiment.

As shown in FIGS. 11, 12 and 13, the operation unit 110 includes joints JT21, JT22, JT23, JT24, JT25, JT26 and JT27. A21, A22, A23, A24, A25, A26 and A27 axes are rotation axes of the joints JT21, JT22, JT23, JT24, JT25, JT26 and JT27.

(Arm)

The arm part 111 includes a link part 111*a*, a link part 111*b* and a link part 111*c*. An upper end side of the link part 111*a* is attached to the remote control apparatus 200 rotatably about the A21 rotation axis extending in a vertical direction. An upper end side of the link part 111*b* is attached to a lower part of the link part 111*a* rotatably about the A22 rotation axis extending in a horizontal direction. One end side of the link part 111*c* is attached to a lower part of the link part 111*b* rotatably about the A23 rotation axis extending in a horizontal direction. The wrist part 112 is attached to another end side of the link part 111*c* rotatably about the A24 rotation axis. The link part 111*a* is connected to the remote control apparatus 200 by the joint JT21. The link part 111*a* is connected to the link part 111*b* by the joint JT22. The link part 111*b* is connected to the link part 111*c* by the joint JT23. The arm part 111 supports the wrist part 112.

The wrist parts 112 include a wrist part 112R shown in FIG. 12 operated by an operator's right hand, and a wrist part 112L shown in FIG. 13 operated by an operator's left hand. A reference posture of the operation unit 110R is shown in FIG. 12, a reference posture of the operation unit 110L is shown in FIG. 13. A configuration of the wrist part 112R is similar to the wrist part 112L.

The wrist part 112 includes a link part 112*a*, a link part 112*b*, a link part 112*c*, and a grip part 112*d* configured to be operated by an operator (e.g., a doctor). The link part 112*a* includes a proximal end connected to a distal end of the arm part 111, and is configured to rotate about an A24 axis. The link part 112*b* includes a proximal end connected to a distal end of the link part 112*a*, and is configured to rotate about an A25 axis. The link part 112*c* includes a proximal end connected to a distal end of the link part 112*b*, and is configured to rotate about an A26 axis. The grip part 112*d* includes a proximal end connected to a distal end of the link part 112*c*, and is configured to rotate about an A27 axis. The link part 112*a*, the link part 112*b* and the link part 112*c* have an L shape. In the reference posture of the operation unit 110, the A24 axis agrees with the A26 axis extend. The A24 axis, the A25 axis, the A26 axis and the A27 axis are orthogonal to each other in the reference posture of the operation unit 110. The A24 axis, the A25 axis, the A26 axis and the A27 axis are an example of a following rotation axis, an example of a first rotation axis, an example of a second rotation axis, and an example of a third rotation axis, respectively. The link part 112*a*, the link part 112*b* and the link part 112*c* are an example of a following link part, an example of a first link part and an example of a second link part, respectively.

Each wrist part 112 includes a pair of grip members 112*e* configured to be opened and closed by the operator. The grip member 112*e* is formed of a thin plate-shaped lever, and near-side ends of the pair of grip members 112*e* are rotatably coupled to a near-side end of the grip part 112*d*. The grip members 112*e* include cylindrical finger insertion sections 112*f*. The operator can insert his or her fingers into the finger insertion sections 112*f*, and operate the wrist part 112. Base-side ends of the pair of grip member 112*e* are coupled to the grip part 112*d* so that opening angle between the Jaw 2*f* and the jaw 2*g* can be changed by increasing/decreasing an angle between the pair of grip members 112*e*. One of the grip members 112*e* includes a magnet, while the grip part 112*d* includes a Hall sensor. The magnet and the Hall sensor function as an angle detection sensor, and can provide an opening angle when the operator opens/closes the grip members 112*e*. One of the grip members 112*e* may include a Hall sensor, while the grip part 112*d* may include a magnet so that they form the angle detection sensor. Also, both the grip members 112*e* may include a magnet or a Hall sensor as a part of the angle detection sensor.

An intersection between rotation axes of operation unit 110 is referred to as gimbal point GP. Specifically, the gimbal point GP is an intersection between the A24 axis, the A25 axis, the A26 axis and the A27 axis. The gimbal point GP is positioned in the grip part 112*d* to which the pair of grip members 112*e* are attached. Each of the operation unit 110L and the operation unit 110R has the gimbal point GP. A gimbal point of the operation unit 110R is defined as GPR. A gimbal point of the operation unit 110L is defined as GPL.

In the reference posture, the A24 axis and the A26 axis of the operation unit 110 extend in the Zb direction. The A25 axis extends in the Xb direction. The A27 axis extends in the Yb direction. As shown in FIG. 12, in the reference posture, the link part 112*a* and the link part 112*b* of the wrist part 112R arranged in an Xb-Zb plane, and is located on an Xb1 side with respect to the A27 axis. In the reference posture, the link part 112*c* arranged in an Yb-Zb plane. In the reference posture, the grip part 112*d* extend in the A27 axis. A rotational position of the link part 112*b* in the reference posture is referred to as a first reference rotational position. A rotational position of the link part 112*c* in the reference posture is referred to as a second reference rotational position.

As shown in FIG. 13, in the reference posture, the link part 112*a* and the link part 112*b* of the wrist part 112L arranged in an Xb-Zb plane, and is located on an Xb2 side with respect to the A27 axis. In the reference posture, the link part 112*c* arranged in an Yb-Zb plane. In the reference posture, the grip part 112*d* extend in the A27 axis.

Figure 14:
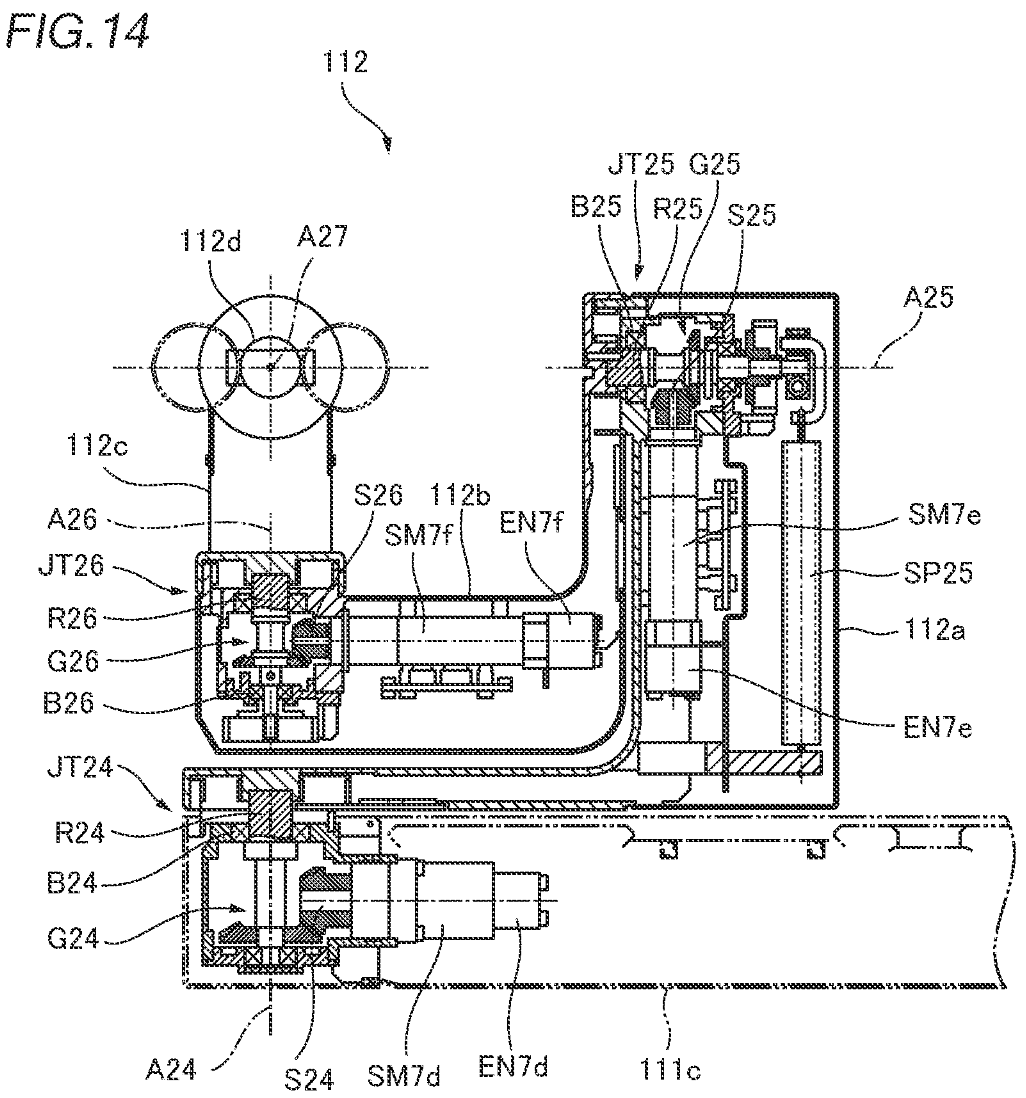
FIG. 14 is a cross-sectional diagram of the wrist part taken along a plane including an A25 axis and an A26 axis.

As shown in FIG. 14, the link part 112*a* has an elbow-shaped (L-shaped) box body, and accommodates main elements of the link part 112*a* in the box body. A rotation axis R24 is positioned in an end part of the link part 112*a*. The rotation axis R24 is held in another end part of the link part 111*c* by a bearing B24 pivotably about the A24 axis. The joint JT24 is constructed of the rotation axis R24 and the bearing B24. Accordingly, the link part 112*a* can pivot about the rotation axis A24 with respect to the link part 111*c*.

A servomotor SM7*d* is arranged in the link part 111*c* so that a center axis of a main shaft S24 is orthogonal to the A24 axis. The encoder EN7*d* for detecting a rotation angle of the servomotor SM7*d* is arranged in the servomotor SM7*d*. Any encoder that can detect the rotation angle can be used as the encoder EN7*d*, or a rotation meter, etc. may be used instead of the encoder EN7*d*. The encoder EN7*d* is directly coupled to the main shaft S24 of the servomotor SM7*d*. The main shaft S24 of the servomotor SM7*d* is coupled to the rotation axis R24 through a bevel gear mechanism G24. Accordingly, the encoder EN7*d* can detect a rotation angle of the servomotor SM7*d* when the link part 112*a* rotates, and the rotation axis R24 can be rotatably driven by the servomotor SM7*d*.

The link part 112*b* has an elbow-shaped (L-shaped) box body, and accommodates main elements of the link part 112*b* in the box body. A rotation axis R25 is positioned in an end part of the link part 112*b*. The rotation axis R25 is held in another end part of the link part 112*a* by a bearing B25 pivotably about the A25 axis. The joint JT25 is constructed of the rotation axis R25 and the bearing B25. Accordingly, the link part 112*b* can pivot about the rotation axis A25 with respect to the link part 112*a*.

A servomotor SM7*e* is arranged in the link part 112*a* so that a center axis of a main shaft S25 is orthogonal to the A25 axis. The encoder EN7*e* for detecting a rotation angle of the servomotor SM7*e* is arranged in the servomotor SM7*e*. A rotation meter, etc. may be used instead of the encoder EN7*e*. The encoder EN7*e* is directly coupled to the main shaft S25 of the servomotor SM7*e*. The main shaft S25 of the servomotor SM7*e* is coupled to the rotation axis R25 through a bevel gear mechanism G25. Accordingly, the encoder EN7*e* can detect a rotation angle of the servomotor SM7*e* when the link part 112*b* rotates, and the rotation axis R25 can be rotatably driven by the servomotor SM7*e*.

A compression coil spring SP25 is arranged between a predetermined part of the link part 112*a* and the rotation axis R25. For example, the predetermined part is a lower end part of a rear end part of the link part 112*a* in the reference posture of the wrist part 112. The compression coil spring SP25 is arranged with its center axis being in parallel to the A24 axis and orthogonal to the A25 axis. Also, the compression coil spring SP25 is designed so that a predetermined torque is applied to the link part 112*b* in a rotating direction when the link part 112*b* pivots from the reference posture of the wrist part 112. The predetermined torque is predetermined to partially cancel a gravity torque applied to the rotation axis R25 by a self weight of parts of the wrist part 112 that include the link part 112*b* and parts on a front side with respect to the link part 112*b*. Accordingly, a part of of the gravity torque applied to the rotation axis R25 is canceled by the compression coil spring SP25.

Figure 15:
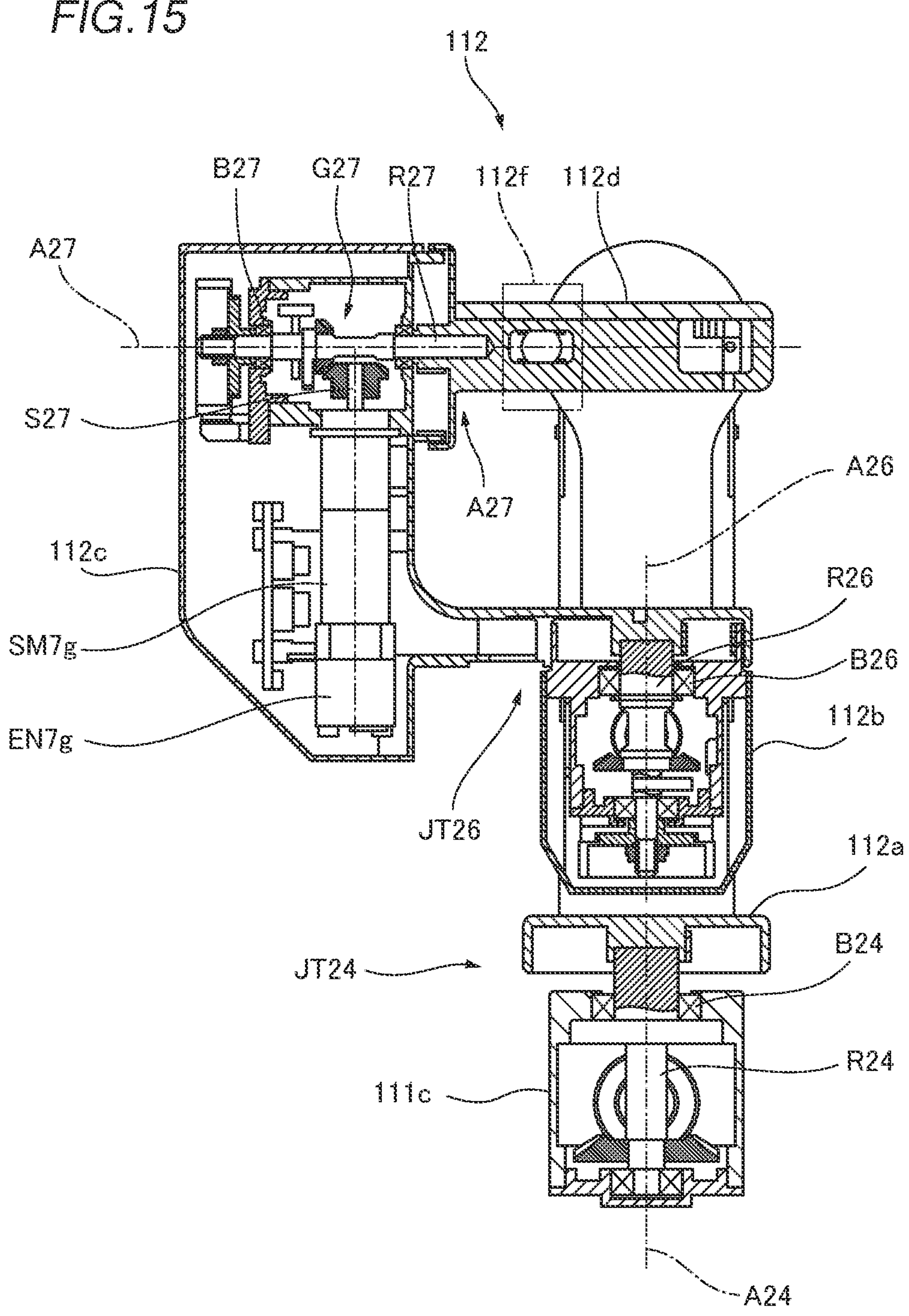
FIG. 15 is a cross-sectional diagram of the wrist part taken along a plane including an A26 axis and an A27 axis.

As shown in FIGS. 14 and 15, the link part 112*c* has an elbow-shaped (L-shaped) box body, and accommodates main elements of the link part 112*c* in the box body. A rotation axis R26 is positioned in an end part of the link part 112*c*. The rotation axis R26 is held in another end part of the link part 112*b* by a bearing B26 pivotably about the A26 axis. The joint JT26 is constructed of the rotation axis R26 and the bearing B26. Accordingly, the link part 112*c* can pivot about the rotation axis A26 with respect to the link part 112*b*.

A servomotor SM7*f* is arranged in the link part 112*b* so that a center axis of a main shaft S26 is orthogonal to the A26 axis. The encoder EN7*f* for detecting a rotation angle of the servomotor SM7*f* is arranged in the servomotor SM7*f*. A rotation meter, etc. may be used instead of the encoder EN7*f*. The encoder EN7*f* is directly coupled to the main shaft S26 of the servomotor SM7*f*. The main shaft S26 of the servomotor SM7*f* is coupled to the rotation axis R26 through a bevel gear mechanism G26. Accordingly, the encoder EN7*f* can detect a rotation angle of the servomotor SM7*f* when the link part 112*c* rotates, and the rotation axis R26 can be rotatably driven by the servomotor SM7*f*.

As shown in FIG. 15, a rotation axis R27 is positioned in an end part of the grip part 112*d*. The rotation axis R27 is held in another end part of the link part 112*c* by a bearing B27 pivotably about the A27 axis. The joint JT27 is constructed of the rotation axis R27 and the bearing B27.

Accordingly, the grip part 112*d* can pivot about the rotation axis A27 with respect to the link part 112*c*.

A servomotor SM7*g* is arranged in the link part 112*c* so that a center axis of a main shaft S27 is orthogonal to the A27 axis. The encoder EN7*g* for detecting a rotation angle of the servomotor SM7*g* is arranged in the servomotor SM7*g*. A rotation meter, etc. may be used instead of the encoder EN7*g*. The encoder EN7*g* is directly coupled to the main shaft S27 of the servomotor SM7*g*. The main shaft S27 of the servomotor SM7*g* is coupled to the rotation axis R27 through a bevel gear mechanism G27. Accordingly, the encoder EN7*g* can detect a rotation angle of the servomotor SM7*g* when the grip part 112*d* rotates, and the rotation axis R27 can be rotatably driven by the servomotor SM7*g*.

As shown in FIG. 1, the monitor 140 is a scope-type display device configured to display images captured by the endoscope 3. The monitor 140 includes an information producer 141. The information producer 141 is configured to produce an error sound. The support arm 150 supports the monitor 140, and can adjust a height of the monitor 140 to a height of eyes of the operator such as doctor. The touch panel 130 is arranged on the support bar 160. When a head of the operator is detected by a sensor arranged in proximity to the monitor 140, the surgical robot 100 can accept manual operations from the remote control apparatus 200. The operator will manually operate the operation unit 110 and the foot pedals 120 while seeing of an affected area on the monitor 140. Instructions can be provided to the remote control apparatus 200 in accordance with these manual operations. Instructions provided to the remote control apparatus 200 are transmitted to the surgical robot 100.

The error reset button 161 is arranged on the support bar 160. The error reset button 161 is configured to reset an error of the robotic surgical system 500. An exemplary error is an error of abnormal deviation.

(Foot Pedal)

Figure 16:
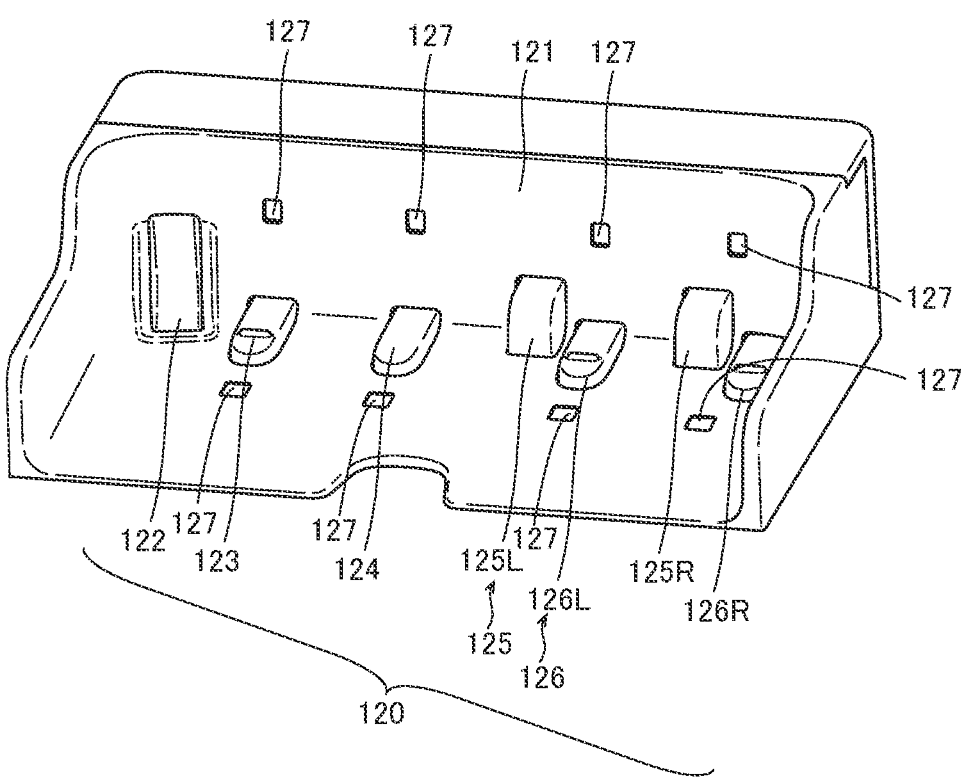
FIG. 16 is a perspective diagram showing a foot pedal according to the one embodiment.

As shown in FIG. 16, a plurality of foot pedals 120 configured to activate functions of the surgical instruments 1. The plurality of foot pedals 120 are provided in a base 121. The foot pedals 120 include a switching pedal 122, a clutch pedal 123, a camera pedal 124, incision pedals 125, coagulation pedals 126, and foot detectors 127. The switching pedal 122, the clutch pedal 123, the camera pedal 124, the incision pedals 125, the coagulation pedals 126 are configured to be operated by an operator's foot. Also, the incision pedals 125 include an incision pedal 125R corresponding to a right-side robot arm 50 and an incision pedal 125L corresponding to a left-side robot arm 50. Also, the coagulation pedals 126 include a coagulation pedal 126R corresponding to a right-side robot arm 50 and a coagulation pedal 126L corresponding to a left-side robot arm 50.

The switching pedal 122 is configured to switch between the robot arms 50 to be operated by the operation unit 110. The clutch pedal 123 is configured to activate a clutch function of temporally halting operation connection between the robot arm 50 and the operation unit 110. While the clutch pedal 123 is pressed by the operator, instructions provided by the operation unit 110 is not transmitted to the robot arm 50. While the camera pedal 124 is pressed by the operator, the robot arm 50 that holds the endoscope 3 can be operated through the operation unit 110. While the incision pedal 125 or the coagulation pedal 126 is pressed, an electric surgical apparatus is active.

The foot detectors 127 are configured to detect the operator's foot that operates the foot pedal 120. The foot detector 127 are arranged corresponding to the switching pedal 122, the clutch pedal 123, the camera pedal 124, the incision pedal 125, the coagulation pedal 126 to detect a foot that hovers above their corresponding foot pedal 120. The foot detectors 127 are arranged on the base 121.

(Vision Unit and Image Processing Unit)

As shown in FIG. 1, a cart 210 holds a vision unit 300 and an image processing unit 400. The image processing unit 400 is configured to process images captured by the endoscope 3. A display 220 is arranged on the cart 210. The display 220 is configured to display images captured by the endoscope 3. An error reset button 230 and an information producer 240 are arranged on a vision unit 300. The error reset button 230 is configured to reset an error of the robotic surgical system 500. An exemplary error is an error of abnormal deviation. The information producer 240 is configured to produce an error sound.

(Configuration of Control System)

As shown in FIG. 17, the robotic surgical system 500 includes a first controller 310, an arm controller 320, a positioner controller 330, operation controllers 340 and a second controller 350. In addition, the robotic surgical system 500 includes a storage 311 connected to the first controller 310, and a storage 351 connected to the second controller 350. The operation controller 340 is an example of a controller.

The first controller 310 is accommodated in the medical cart 10, and configured to communicate with the arm controller 320 and the positioner controller 330 so that the robotic surgical system 500 is entirely controlled. Specifically, the first controller 310 is configured to control the arm controller 320, the positioner controller 330 and the operation controllers 340 by using the communications with them. The first controller 310 is connected to the arm controller 320, the positioner controller 330 and the operation controllers 340 through LAN, etc. The first controller 310 is arranged in the medical cart 10.

Each of the plurality of robot arms 50 includes the arm controller 320. In other words, a plurality of arm controllers 320 the number of which corresponds to the number of the plurality of robot arms 50 are included in the medical cart 10.

As shown in FIG. 17, the input 22 is connected to the first controller 310 through LAN, etc. The status indicator 41, the arm status indicator 42, the operating handle 23, the throttle grip 23*a*, the joystick 22*b*, the stabilizer 24 and the electric cylinder 25 are connected to the positioner controller 330 through a wiring line 360 by means of a communication network that can share information with them by using serial communication. Although all these status indicators 41, arm status indicator 42, etc. are connected to each other through one wiring line 360 in FIG. 17, wiring lines 360 are actually provided to each of the status indicator 41, the arm status indicator 42, the operating handle 23, the throttle grip 23*a*, the joystick 22*b*, the stabilizer 24 and the electric cylinder 25.

Figures 18, 19:
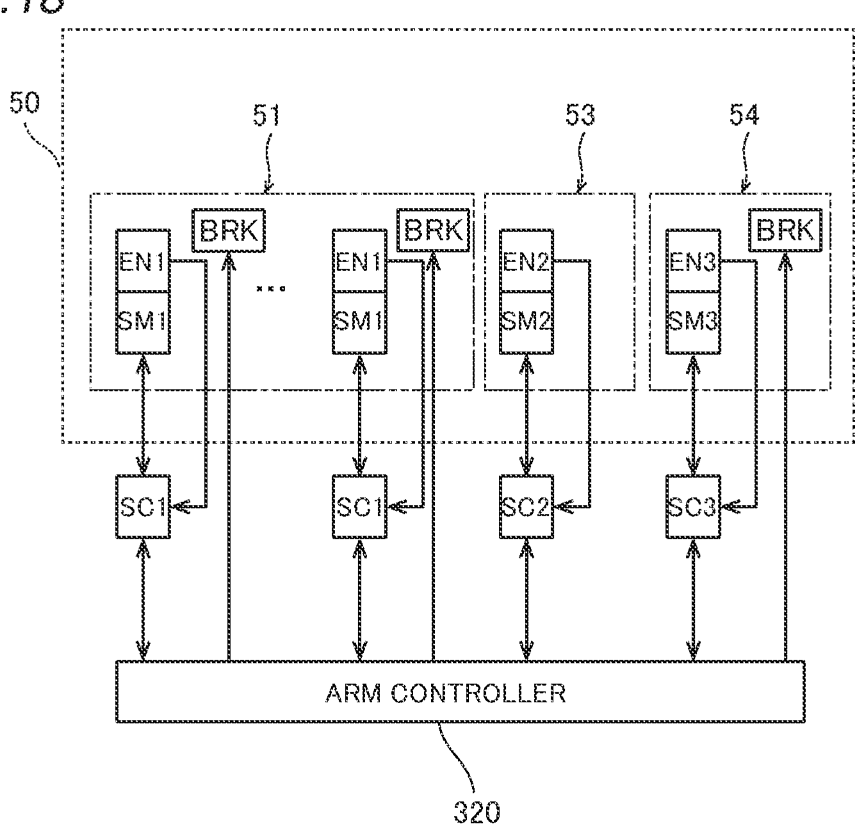
FIG. 18 is a control block diagram of the robot arm according to the one embodiment.
FIG. 19 is a control block diagram of a positioner and the medical cart according to the one embodiment.

As shown in FIG. 18, each arm 51 includes a plurality of servomotors SM1, a plurality of encoders EN1 and a plurality of speed reducers corresponding to the plurality of joints JT1, JT2, JT3, JT4, JT5, JT6 and JT7. The encoder EN1 is configured to detect a rotation angle of the servomotor SM1. The speed reducer is configured to reduce a rotation of the servomotor SM1 whereby increasing its torque. A servo controller SC1 is configured to control the servomotor SM1, and is arranged in the medical cart 10 adjacent to the arm controller 320. Also, the encoder EN1 is configured to detect the rotation angle of the servomotor SM1, and is electrically connected to the servo controller SC1.

The second link part 53 includes a servomotor SM2 configured to rotate a driven member arranged in a driven unit 2*a* of the surgical instrument 1, an encoder EN2, and a speed reducer. The encoder EN2 is configured to detect a rotation angle of the servomotor SM2. The speed reducer is configured to reduce a rotation of the servomotor SM2 whereby increasing its torque. The medical cart 10 includes a servo controller SC2 configured to control the servomotor SM2 for driving the surgical instrument 1. The encoder EN2 for detecting the rotation angle of the servo motor SM2 is electrically connected to the servo control unit SC2. Note that a plurality of servomotors SM2, a plurality of encoders EN2 and a plurality of servo controllers SC2 are included.

The translation mechanism 54 includes a servomotor SM3 configured to translationally move the surgical instrument 1, an encoder EN3, and a speed reducer. The encoder EN3 is configured to detect a rotation angle of the servomotor SM3. The speed reducer is configured to reduce a rotation of the servomotor SM3 whereby increasing its torque. The medical cart 10 includes a servo controller SC3 configured to control the servomotor SM3 for translationally moving the surgical instrument 1. The encoder EN3 for detecting the rotation angle of the servo motor SM3 is electrically connected to the servo control unit SC3.

The first controller 310 is configured to generate instruction values that specify positions of the servomotor SM1, SM2 and SM3 in accordance with manual operation that is received by the remote control apparatus 200, and to drive the servomotor SM1, SM2 and SM3 in accordance with the instruction values. If any of differences between instruction values and positions of servomotor SM1, SM2 and SM3 detected by sensors becomes greater than an allowable range, the first controller 310 determines an error of abnormal deviation.

As shown in FIG. 19, the positioner 30 includes a plurality of servomotors SM4, a plurality of encoders EN4 and a plurality of speed reducers corresponding to a plurality of joints 33 of the positioner 30. Each encoder EN4 is configured to detect a rotation angle of the servomotor SM4. The speed reducer is configured to reduce a rotation of the servomotor SM4 whereby increasing its torque.

The medical cart 10 includes wheels including front wheels as driving wheels, and rear wheels configured to be steered by manually operating the handle 23. The rear wheels are arranged closer to the operating handle 23 with respect to the front wheels. The medical cart 10 includes a servomotor SM5 configured to drive the front wheels of the medical cart 10, an encoder EN5, speed reducers, and brakes BRK. The speed reducer is configured to reduce a rotation of the servomotor SM5 whereby increasing its torque. Also, the operating handle 23 of the medical cart 10 includes a potentiometer P1 shown in FIG. 3, and the servomotor SM5 of the front wheels can be driven in accordance with a rotation angle detected by the potentiometer P1 in response to a twisting amount of the throttle grip 23*a*. The rear wheels of the medical cart 10 have a twin-wheel type structure, and the rear wheels can be steered in accordance with a rightward/leftward turn of the operating handle 23. Also, the operating handle 23 of the medical cart 10 includes a potentiometer P2 shown in FIG. 3 on a turning shaft, and the rear wheel of the medical cart 10 is provided with a servomotor SM6, an encoder EN6, and speed reducers. The speed reducer is configured to reduce a rotation of the servomotor SM6 whereby increasing its torque. The servomotor SM6 can be driven in accordance with a rotation angle detected by the potentiometer P2 in response to a rightward/leftward turning amount of the operating handle 23. In other words, power is assisted by the servomotor SM6 when the rear wheels are steered by turning the operating handle 23 rightward or leftward.

The medical cart 10 can be moved forward or rearward by driving the front wheels. Also, the medical cart 10 can be turned rightward or leftward by steering the rear wheels by turning the operating handle 23 of the medical cart 10.

As shown in FIG. 19, the medical cart 10 includes servo controllers SC4 configured to control the servomotors SM4 for moving the positioner 30. Also, the encoder EN4 is configured to detect the rotation angle of the servomotor SM4, and is electrically connected to the servo controller SC4. The medical cart 10 includes a servo controller SC5 configured to control the servomotor SM5 for driving the front wheels of the medical cart 10. The encoder EN5 for detecting the rotation angle of the servo motor SM5 is electrically connected to the servo control unit SC5. The medical cart 10 includes a servo controller SC6 configured to control the servomotor SM6 for power assistance to steering of the rear wheels of the medical cart 10. The encoder EN6 for detecting the rotation angle of the servo motor SM6 is electrically connected to the servo control unit SC6.

As shown in FIGS. 18 and 19, the joints JT1, JT2, JT3, JT4, JT5, JT6 and JT7 of the arm 51, and the joints 33 of the positioner 30 include their brake BRK. Also, the front wheels of the medical cart 10, the arm base 40 and the translation mechanism 54 include their brake BRK. The arm controller 320 is configured to one-directionally transmit control signals to the brakes BRK of the joints JT1, JT2, JT3, JT4, JT5, JT6 and JT7 of the arm 51, and the translation mechanism 54. The control signals are configured to indicate ON/OFF of the brakes BRK. The signals indicating on of the brakes BRK include a signal that instructs the brake BRK to keep activating. The control signals transmitted from the positioner controller 330 to the brakes BRK included in the joints 33 of the positioner 30 and the arm base 40 are configured similar to the control signals transmitted from the arm controller. On startup, all the brakes BRK of the arm base 40, the arm 51 and the translation mechanism 54 are turned off but the servomotors SM are driven to keep postures of the robot arm 50 and the arm base 40 against gravity. If an error occurs in the robotic surgical system 500, the brakes BRK included in the arm base 40, the arm 51 and the translation mechanism 54 are turned on. When the error in the robotic surgical system 500 is reset, the brakes BRK included in the arm base 40, the arm 51 and the translation mechanism 54 are turned off. When shutdown operation is performed in the robotic surgical system 500 is reset, the brakes BRK included in the arm base 40, the arm 51 and the translation mechanism 54 are turned on. The brakes BRK of the front wheels of the medical cart 10 are constantly turned on, and the brakes BRK are deactivated only when the enable switch 23*b* of the medical cart 10 is kept pressed. Also, the brakes BRK of the joints 33 of the positioner 30 are constantly turned on, and the brakes BRK are deactivated only when the enable switch 22*c* of the medical cart 10 is kept pressed.

Figure 20:
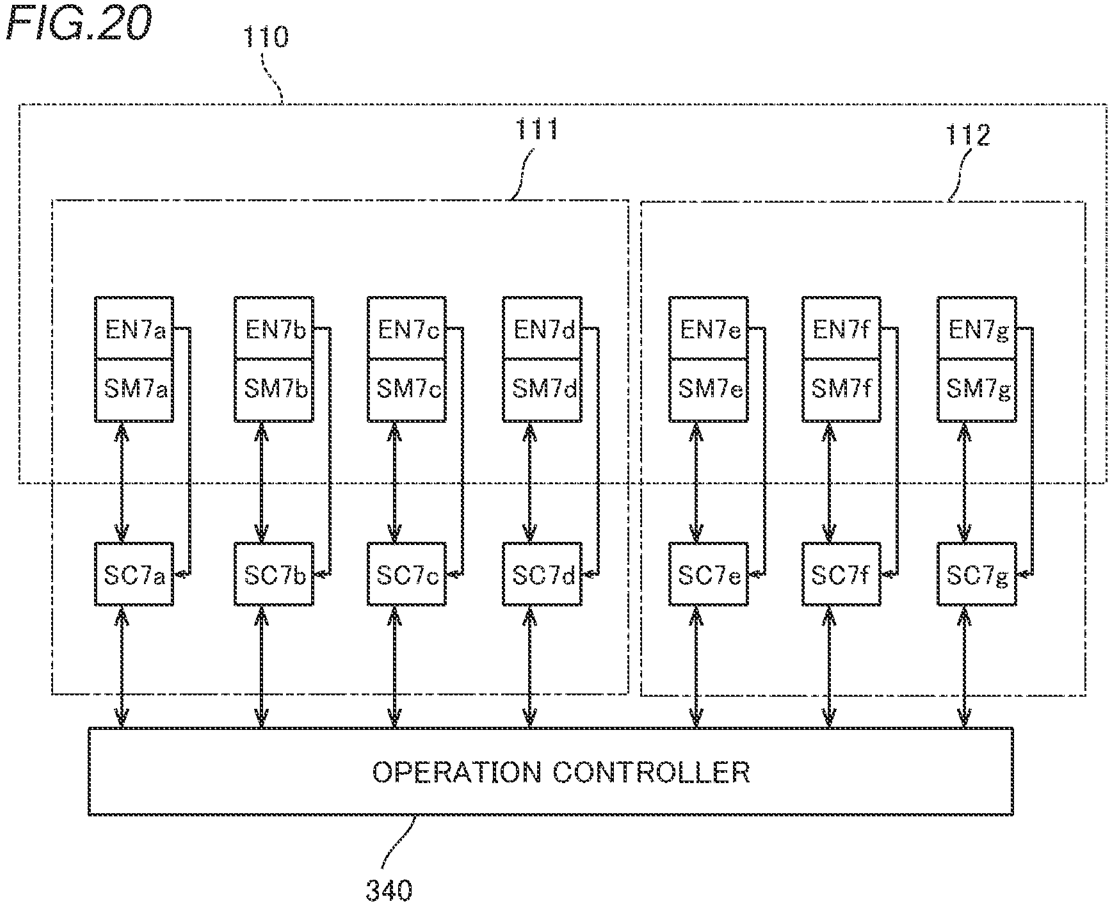
FIG. 20 is a control block diagram of the operation unit according to the one embodiment.

As shown in FIG. 20, the joints JT21, JT22, JT23, JT24, JT25, JT26 and JT27 of the operation unit 110 includes servomotors SM7*a*, SM7*b*, SM7*c*, SM7*d*, SM7*e*, SM7*f* and SM7*g*, respectively. Also, servo controllers SC7*a*, SC7*b*, SC7*c*, SC7*d*, SC7*e*, SC7*f* and SC7*g* configured to control the servomotors are provided. Encoder EN7*a*, EN7*b*, EN7*c*, EN7*d*, EN7*e*, EN7*f* and EN7*g* for detecting rotation angles of the servomotors are electrically connected to the servo controllers. Each of the operation unit 110L and the operation unit 110R includes the servomotors, the servo controllers, and the encoders. The servomotor SM7*d* is an example of a driver.

The first controller 310 is configured to control the servomotors through the operation controllers 340 so that torques are produced to cancel out gravitational torques applied to the rotation axes of the servomotors in postures of the operation units 110. Accordingly, the operator can manually operate the operation units 110 by relatively small forces.

The first controller 310 is configured to control the servomotors in accordance with manipulations of the operation units 110 through the operation controllers 340 so that torques are produced onto the rotation axes of the servomotors to assist the operator in his or her operation. Accordingly, the operator can manually operate the operation units 110 by relatively small forces.

As shown in FIG. 17, the first controller 310 is configured to control the robot arm 50 in accordance with manual operations received by the arm operation unit 60. For example, the first controller 310 is configured to control the robot arm 50 in accordance with manual operations received by the joystick 62 of the arm operation unit 60. Specifically, the arm controller 320 provides an input signal provided from the joystick 62 to the first controller 310. The first controller 310 generates position instructions based on the received input signal and the rotation angles detected by the encoders EN1, and provides the position instructions to the servo controllers SC1 via the arm controller 320. The servo controllers SC1 generate current instructions based on the position instructions provided from the arm controller 320 and the rotation angles detected by the encoders EN1, and provide the current instructions to the servomotors SM1. Accordingly, the robot arm 50 is moved in accordance with an operation instruction provided to the joystick 62.

The first controller 310 controls the robot arm 50 based on an input signal from the linear switch 63 of the arm operation unit 60. Specifically, the arm controller 320 provides an input signal provided from the linear switch 63 to the first controller 310. The first controller 310 generates position instructions based on the received input signal and the rotation angles detected by the encoder EN1 or EN3, and provides the position instructions to the servo controller SC1 or SC3 via the arm controller 320. The servo controller SC1 or SC3 generate current instructions based on the position instructions provided from the arm controller 320 and the rotation angles detected by the encoder EN1 or EN3, and provide the current instructions to the servomotor SM1 or SM3. Accordingly, the robot arm 50 is moved in accordance with an operation instruction provided to the linear switch 63.

The medical cart 10 includes the positioner controller 330. The positioner controller 330 is configured to control the positioner 30 and the medical cart 10. The positioner 30 includes a plurality of servomotors SM4, a plurality of encoders EN4 and a plurality of speed reducers corresponding to a plurality of joints 33 of the positioner 30. The medical cart 10 includes the servo controllers SC4 configured to control the servomotors SM4 of the positioner 30. The medical cart 10 includes servomotors SM5 and SM6 configured to drive the front wheels of the medical cart 10, the encoders EN5 and EN6, speed reducers, the servo controllers SC5 and SC6, and brakes BRK.

The operation controllers 340 are provided in a main body of the remote control apparatus 200. The operation controllers 340 are configured to control the operation units 110. The operation controllers 340 are associated with both the left-hand side operation unit 110L and the right-hand side operation unit 110R as shown in FIG. 17. The operation unit 110 includes servomotors SM, encoders EN and speed reducers corresponding to the plurality of joints JT21 to JT27 of the operation unit 110. The servo controllers SC configured to control the servomotors SM of the operation unit 110 is provided in the main body of the remote control apparatus 200 adjacent to the operation controllers 340.

As shown in FIG. 17, the vision unit 300 and the image processing unit 400 are connected to the first controller 310 through LAN. The display 220 is connected to the vision unit 300.

(Description of Interference)

As shown in FIG. 12, the link part 112*a* is arranged in a plane including the A24 and A25 axes orthogonal to each other. The link part 112*b* is arranged in a plane including the A25 and A26 axes orthogonal to each other. The link part 112*c* is arranged in a plane including the A26 and A27 axes orthogonal to each other. When the link part 112*c* rotates from this position to a position in proximity to the link part 112*b*, a lower end LE of the link part 112*c* interferes with the link part 112*b*.

To address this, in this embodiment, the operation controller 340 is configured to execute following control in which the link part 112*a* is rotated about the A24 axis based on a rotational position of the link part 112*c* by the servomotor SM7*d* to keep an angle formed by the link part 112*c* and the link part 112*b* at a predetermined angle. For example, the predetermined angle is 90 degrees. The following description describes a method of generating instruction values in detail.

(Description of Interference Prevention)

Figure 21:
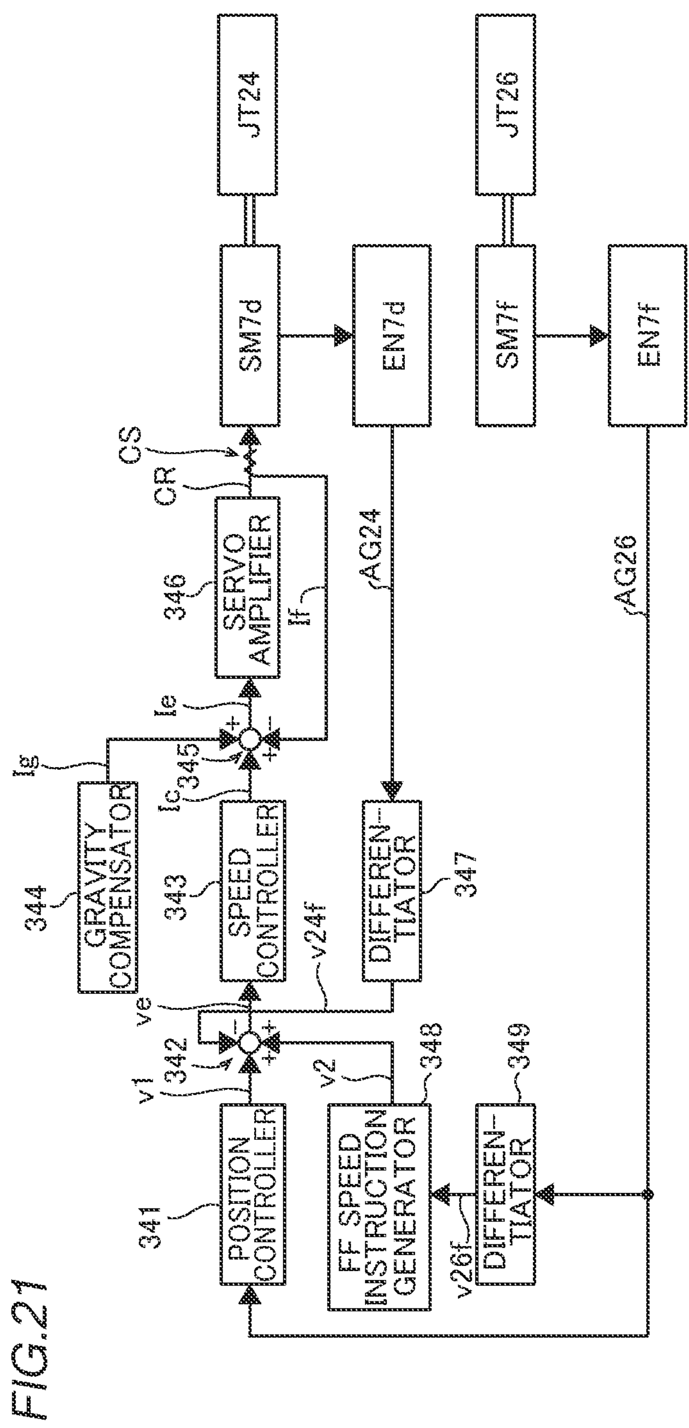
FIG. 21 is a block diagram showing a configuration for executing following control.

As shown in FIG. 21, the operation controller 340 includes a position controller 341, an adder/subtractor 342, a speed controller 343, a gravity compensator 344, an adder/subtractor 345, a servo amplifier 346, a differentiator 347, an FF speed instruction generator 348 and a differentiator 349.

The position controller 341, the adder/subtractor 342, the speed controller 343, the gravity compensator 344, the adder/subtractor 345, the differentiator 347, the FF speed instruction generator 348 and the differentiator 349 can be constructed by using an arithmetic unit having including a processor and a memory, for example. For example, the processor is a microcontroller, etc. Also, for example, the processors can include a CPU, an MPU, an FPGA (Field Programmable Gate Array), Programmable Logic Controller (PLC), etc. The memory is a processor internal memory such as a ROM and a RAM, or an external memory such as a hard disk drive.

The position controller 341, the adder/subtractor 342, the speed controller 343, the gravity compensator 344, the adder/subtractor 345, the differentiator 347, the FF speed instruction generator 348 and the differentiator 349 are functional blocks implemented by reading a predetermined control program stored in the memory of the arithmetic unit and executing the program by using the processor of the arithmetic unit. Specifically, the arithmetic unit serves as the position controller 341, the adder/subtractor 342, the speed controller 343, the gravity compensator 344, the adder/subtractor 345, the servo amplifier 346, the differentiator 347, the FF speed instruction generator 348 and the differentiator 349.

The position controller 341, the adder/subtractor 342, the speed controller 343, the gravity compensator 344, the adder/subtractor 345, the differentiator 347, the FF speed instruction generator 348 and the differentiator 349 may be constructed of hardware such as electronic circuits.

(Gravity Compensation)

A configuration for gravity compensation is now described. The gravity compensator 344 is configured to determine a posture of the operation unit 110 based on the rotation angles AG of the servo motors SM7*a*, SM7*b*, SM7*c*, SM7*d*, SM7*e*, SM7*f* and SM7*g* accepted by the operation unit 110. The gravity compensator 344 is configured to calculate gravitation-canceling torques that cancel gravitational torques produced on the joints JT21, JT22, JT23, JT24, JT25, JT26 and JT27. The gravity compensator 344 can provide gravity compensation amounts that cancel the gravitational torques produced on the joints JT21, JT22, JT23, JT24, JT25, JT26 and JT27 as a gravity compensation current instruction Ig.

(Prevention Control for Interference of Link Parts)

A configuration that controls prevention of interference of the link part 112*a* is now described. When the grip part 112*d* is operated so that the link part 112*c* is rotated about the A26 axis, the servomotor SM7*f* of joint JT26 rotates. The encoder EN7*f* is configured to detect the rotation of the servomotor SM7*f* and to provide a rotation angle AG26 detected. The position controller 341 is configured to calculate a deviation of the rotation angle AG26 from the second reference rotational position and to convert the deviation into a speed instruction v1.

The differentiator 349 generates a rotational angular speed vf26 by differentiating the rotation angle AG26 provided from the encoder EN7*f*. The FF speed instruction generator 348 is configured to generate a speed instruction v2 for feed-forward control based on a rotational angular speed vf26.

The encoder EN7*d* is configured to detect the rotation of the servomotor SM7*d*, which is configured to drive the link part 112*a*, and to provide a rotation angle AG24 detected. The differentiator 347 differentiates the rotation angle AG24 and outputs the feedback rotation angle velocity vf24.

The adder/subtractor 342 adds the speed instruction v2 for feed-forward control to the speed instruction v1, and subtracts the feedback angular speed vf24 from the added value to produce a speed deviation ve. The speed controller 343 is configured to generate a current instruction Ic in accordance with the speed deviation ve.

A current sensor cs is configured to detect a drive current CR supplied by a servo amplifier 346 and to provide the detected drive current CR as a feedback current If to the adder/subtractor 345. The adder/subtractor 345 adds the gravity compensation current instruction Ig to the current instruction Ic, and subtracts the feedback current If from the added value to produce a current deviation Ie. The servo amplifier 346 provides the drive current CR to the servo motor SM7*d* in accordance with on the current deviation Ie. The servo motor SM7*d* drives its corresponding link part in accordance with on the drive current CR. Accordingly, the link part 112*a* is rotated to keep an angle formed by the link part 112*c* and the link part 112*b* at a predetermined angle. For example, the predetermined angle is 90 degrees. Control of rotation of the link part 112*a* executed by the operation controller 340 to keep an angle formed by the link part 112*c* and the link part 112*b* at the predetermined angle is referred to as following control.

(Position Controller)

Figure 22:
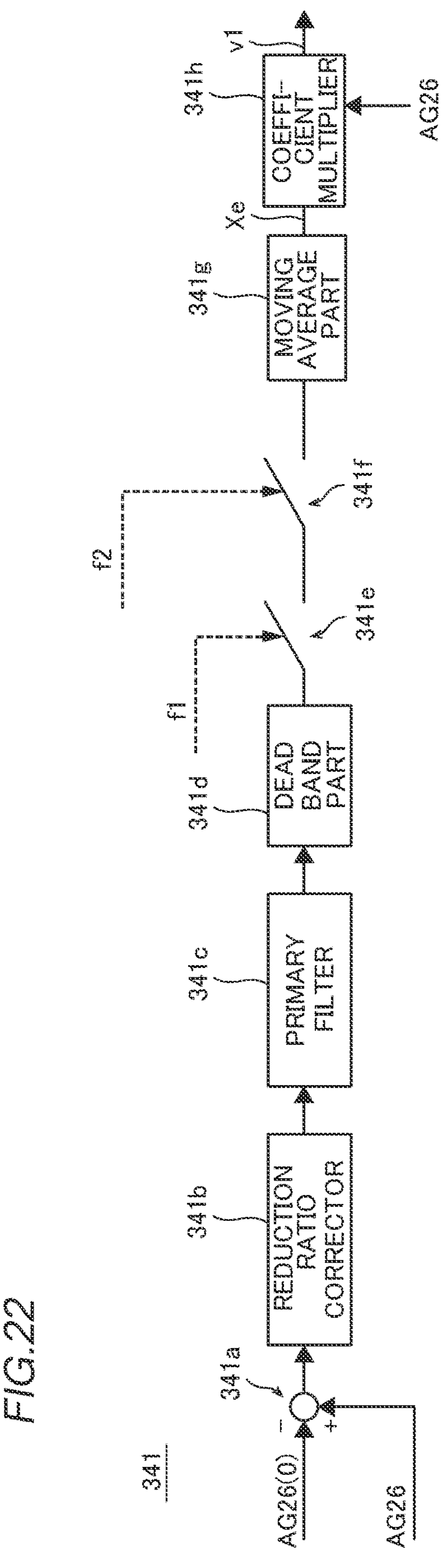
FIG. 22 is a block diagram showing a configuration of a position controller.

As shown in FIG. 22, the position controller 341 includes a subtractor 341*a*, a reduction ratio corrector 341*b*, a primary filter 341*c*, and a dead band part 341*d*, a first switch 341*e*, a second switch 341*f*, a moving average part 341*g*, and a coefficient multiplier 341*h*.

The subtractor 341*a* subtracts a rotation angle AG26 (0) of the second reference rotational position of the link part 112*c* from the rotation angle AG26 provided from the encoder EN7*f* to produce a rotational position deviation of the link part 112*c*. The rotation angle AG26 (0) of the second reference rotational position is 0 degree.

The reduction ratio corrector 341*b* is configured to apply reduction ratio correction to the rotational position deviation of the joint JT26, and to convert the rotational position deviation of the joint JT26 to a rotational position deviation corresponding to the reduction ratio of the joint JT24. A reduction ratio of the joint JT26 and the reduction ratio of the joint JT24 are different from each other. For this reason, a rotation angle AG26 that is detected by the encoder EN7*f* when the link part 112*c* rotates one revolution in the joint JT26 is different from a rotation angle AG24 that is detected by the encoder EN7*d* when the link part 112*a* rotates one revolution in the joint JT24. Specifically, where the reduction ratio of the joint JT26 is RR26, and the reduction ratio of the joint JT24 is RR24, 1/RR26, which is the reciprocal of the reduction ratio RR26 of the joint JT26, and 1/RR24, which is the reciprocal of the reduction ratio RR24 of the joint JT24, make the rotation angle AG26 and the rotation angle AG24 different from each other. Correspondingly, the reduction ratio corrector 341*b* multiplies the rotational position deviation of the joint JT26 by RR26/RR24 to convert the rotational position deviation of the joint JT26 to a rotational position deviation corresponding to the reduction ratio of the joint JT24.

Subsequently, the primary filter 341*c* is configured to remove high frequency components from the rotational position deviation converted by the reduction ratio corrector 341*b*. Because such high frequency components are different depending on types of operation units 110, a time constant of the primary filter 341*c* may be adjusted depending on the types of operation units 110. In this case, a desired time constant may be accepted by an input (not shown), for example.

Subsequently, the rotational position deviation from which the high-frequency components are removed by the primary filter 341*c* is provided to the dead band part 341*d*. The dead band part 341*d* prevents chattering in a case in which an operation on the link part 112*c* is small so that the provided rotational position deviation is small. The rotational position deviation provided from the dead band part 341*d* is provided to the first switch 341*e* and the second switch 341*f*. The first switch 341*e* is brought in ON if a user-operating flag f1 is ON, and is brought in OFF if the user-operating flag f1 is OFF. The second switch 341*f* is brought in ON if an operation range flag f2 is ON, and is brought in OFF if the operation range flag f2 is OFF.

The user-operating flag f1 indicates that the grip part 112*d* is operated. If a difference between the rotational position of the link part 112*c* in previous sampling and the rotational position of the link part 112*c* in the current sampling is greater than a predetermined change threshold, the operation controller 340 determines that the operation unit 110 is being operated. The reason to use the user-operating flag f1 is as follows. For example, the predetermined change threshold is 1.0 degree.

As described above, when the link part 112*c* is rotated by operating the grip part 112*d* by the operator, the link part 112*a* is rotated to position the link part 112*c* at the second reference rotational position. If the operator stops the operation on the grip part 112*d*, the link part 112*a* will keep rotating if a small rotational position deviation of the link part 112*c* still exists. For this reason, the operator feels wrongness. To address this, when the grip part 112*d* is operated, the user-operating flag f1 is turned ON so that feedback control of the rotational position of the link part 112*a* is executed. When the operation on the grip part 112*d* is stopped, the user-operating f1 is turned OFF to stop the feedback control of the rotational position deviation of the link part 112*a* so that the link part 112*a* is stopped. Accordingly, it is possible to prevent that the operator feels wrongness.

The operation range flag f2 indicates that the link part 112*a* is within a predetermined operation range. Because a movable range of the link part 112*a* is defined based on structural limits, following instructions necessarily avoid that the link part 112*a* is out of the movable range. To prevent interference between the link part 112*a* and the link part 112*b*, a rotation range is defined as the operation range within which the following link part 112*a* must be positioned. The operation range flag f2 may be used as necessary even if a movable range of the link part 112*a* is not defined based on structural limits. The operation range can be appropriately defined based on the specifications of the operation unit 110.

The moving average part 341*g* uses a method of moving averages for the rotational position deviation provided through the first switch 341*e* and the second switch 341*f*. Accordingly, it is possible to reduce discontinuity of rotational position deviation, which will appear when the first switch 341*e* or the second switch 341*f* is turned ON/OFF. The speed instruction v1 is generated by multiplying an average of rotational position deviation Xe, which is obtained by the method of moving averages, by a predetermined gain.

Figure 23:
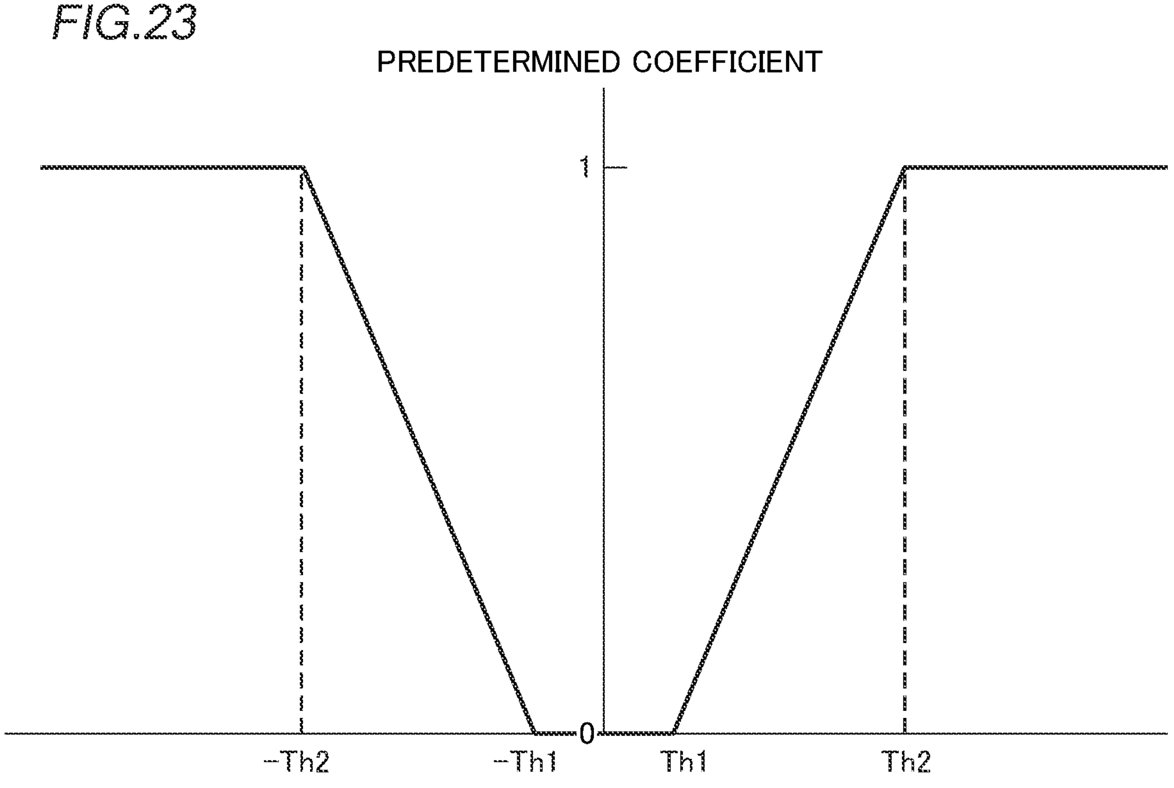
FIG. 23 is a diagram illustrating a relationship between first and second thresholds, and a predetermined coefficient.

In this embodiment, a rotation amount of the link part 112*a* about the A24 axis in the following control in a case in which an absolute value of a moving speed of a gimbal point GP of the operation unit 110 is smaller than predetermined thresholds is smaller than in a case in which the absolute value is not smaller than the predetermined thresholds. As shown in FIG. 23, the predetermined thresholds include a first threshold Th1, and a second threshold Th2 whose absolute value is greater than the first threshold Th1. The operation controller 340 is configured to calculate the moving speed of the gimbal point GP from changes of coordinates of the gimbal point GP obtained from axis values of the operation unit 110, and to set a coefficient by which the rotational position deviation Xe is multiplied to zero if the absolute value of the moving speed of the gimbal point GP of the operation unit 110 is smaller than the first threshold Th1. Accordingly, the rotation amount of the link part 112*a* in the following control can be zero. The operation controller 340 is configured to increase the coefficient by which the rotational position deviation Xe is multiplied with increase of the moving speed of the gimbal point GP of the operation unit 110 whereby increasing the rotation amount of the link part 112*a* from zero to a predetermined rotation amount in the following control if the absolute value of the moving speed of the gimbal point GP of the operation unit 110 is not smaller than the first threshold Th1 and smaller than the second threshold Th2. The operation controller 340 is configured to set the rotation amount of the link part 112*a* to the predetermined rotation amount in the following control if the absolute value of the moving speed of the gimbal point GP of the operation unit 110 is not smaller than the second threshold Th2. For example, the first threshold Th1 is a value falling within a range not smaller than 20 mm/s and not greater than 30 mm/s with respect to a speed of the gimbal point GP of the operation unit 110. For example, the second threshold Th2 is a value falling within a range not smaller than 100 mm/s and not greater than 150 mm/s with respect to a speed of the gimbal point GP of the operation unit 110.

Specifically, in this embodiment, the operation controller 340 is configured to execute the following control based on a value obtained by multiplying the rotational position deviation Xe based on a deviation between the second reference rotational position and the current rotational position of the link part 112*c* by a predetermined coefficient. The multiplication by a predetermined coefficient is executed by the coefficient multiplier 341*h*. The predetermined coefficient in a case in which the absolute value of the moving speed of the gimbal point GP of the operation unit 110 is smaller than the predetermined threshold is smaller than in a case in which the absolute value is not smaller than the predetermined threshold. Specifically, the predetermined coefficient is set to zero when the absolute value of the moving speed of the gimbal point GP of the operation unit 110 is smaller than the first predetermined threshold Th1. The predetermined coefficient is linearly increased from 0 to 1 with increase of the moving speed of the gimbal point GP of the operation unit 110 if the absolute value of the moving speed of the gimbal point GP of the operation unit 110 is not smaller than the first threshold Th1 and smaller than the second threshold Th2. The predetermined coefficient is set to 1 when the absolute value of the moving speed of the gimbal point GP of the operation unit 110 is not smaller than the second predetermined threshold Th2.

(Configuration of FF Speed Instruction Generator 348)

Figure 24:
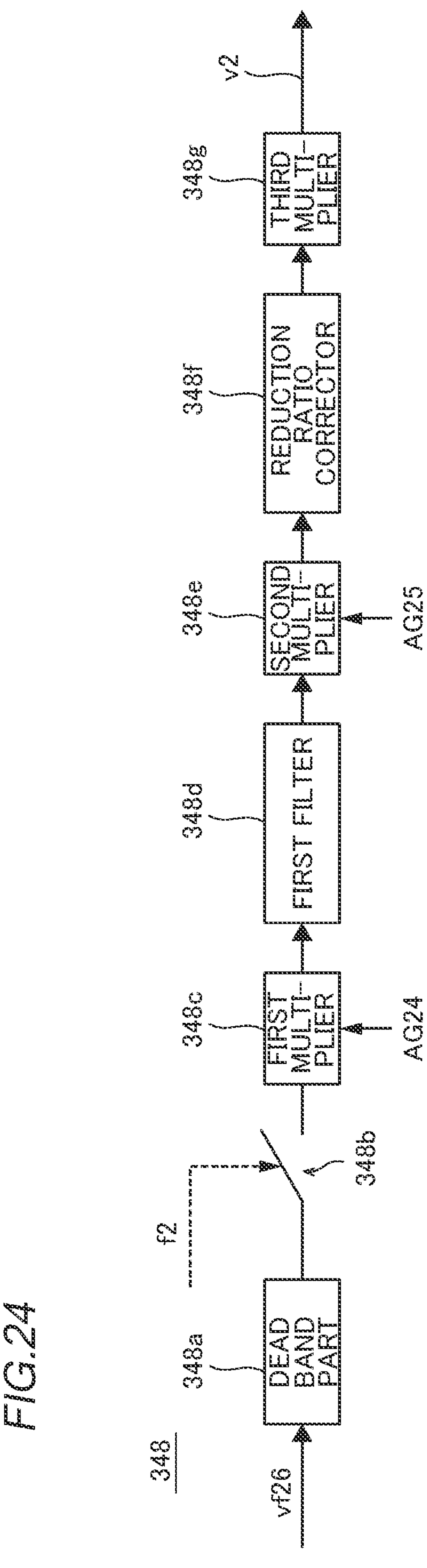
FIG. 24 is a block diagram showing a configuration of an FF speed instruction generator.

As shown in FIG. 24, the FF speed instruction generator 348 includes a dead band part 348*a*, a third switch 348*b*, a first multiplier 348*c*, a primary filter 348*d*, a second multiplier 348*e*, a reduction ratio corrector 348*f*, and a third multiplier 348*g*.

The rotational angular speed vf26 of the link part 112*c* provided from the differentiator 349 is provided to the dead band part 348*a*. The dead band part 348*a* is configured to disable speed feed-forward control if a moving speed of the grip part 112*d* when being operated is slow, or if the rotational angular speed vf26 is small. The rotational angular speed vf26 provided from the dead band part 348*a* is provided to the third switch 348*b*. The third switch 348*b* is brought in ON if an operation range flag f2 is ON, and is brought in OFF if the operation range flag f2 is OFF.

Figure 25:
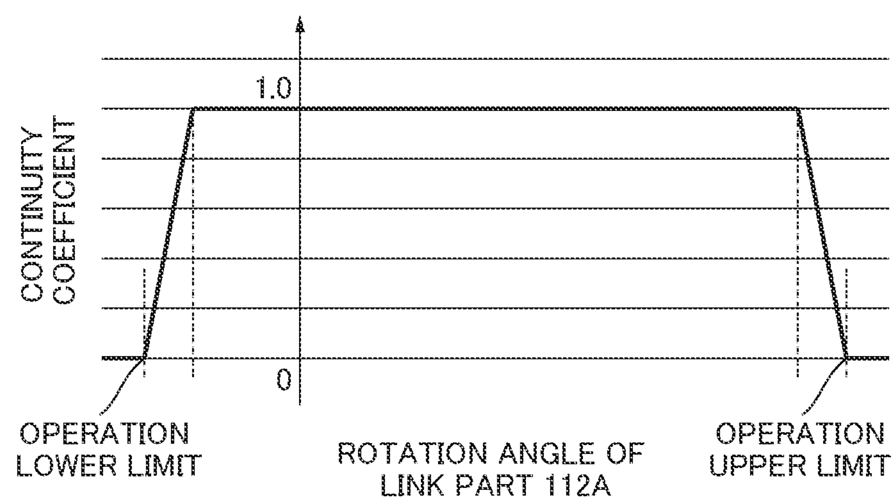
FIG. 25 is a diagram illustrating a relationship between a rotation angle of a link part 112*c* and a continuity coefficient.

The first multiplier 348*c* multiplies the rotational angular speed vf26 provided through the third switch 348*b* by the continuity coefficient. FIG. 25 is a graph illustrating a relationship between a rotation angle of the link part 112*a* and the continuity coefficient. The continuity coefficient is a first adjustment coefficient for adjusting a value provided from the speed feed-forward control to a position feedback control loop. In FIG. 25, a horizontal axis indicates the rotation angle of the link part 112*a*, and a vertical axis indicates the continuity coefficient.

As shown in FIG. 25, the continuity coefficient is a value ranging from 0 to 1.0. For example, the continuity coefficient increases from 0 to 1 with increase of the rotation angle of the link part 112*a* in a range close to an operation lower limit of the link part 112*a*. The continuity coefficient is kept at a constant 1.0 until the rotation angle of the link part 112*a* becomes close to an operation upper limit. The continuity coefficient decreases from 1.0 to 0 with increase of the rotation angle of the link part 112*a* in a range close to the operation upper limit. Although the continuity coefficient linearly changes in ranges close to the operation lower limit and the operation upper limit of the link part 112*a* in FIG. 25, the continuity coefficient may change in a curve as long as it monotonously changes.

As shown in FIG. 24, the rotation angle AG24 of the link part 112*a* detected by the encoder EN7*d* of the joint JT24 is provided to the first multiplier 348*c*. The first multiplier 348*c* determines the continuity coefficient based on the provided rotation angle AG24, and multiplies the rotational angular speed vf26 provided through the third switch 348*b* by the determined continuity coefficient.

Accordingly, when the link part 112*a* rotates from a range outside the operation lower limit into the operation range, the third switch 348*b* is turned ON so that the rotational angular speed vf26 increases from zero. Also, when the link part 112*a* rotates from a range outside the operation upper limit into the operation range, the third switch 348*b* is turned ON so that the rotational angular speed vf26 increases from zero. In other words, when the link part 112*a* rotates from the range outside the operation range into the operation range, an input of the speed feed-forward control provided to the position feedback control loop can have continuity. As a result, it is possible to prevent that the input of the speed feed-forward control provided to the position feedback control loop rapidly changes in the feed-forward control when the link part 112*a* rotates from the range outside the operation range into the operation range, and that the operator feels wrongness.

The primary filter 348*d* is configured to remove high frequency components from the rotational angular speed vf26 that is multiplied by the continuity coefficient. Because such high frequency components are different depending on types of operation units 110, a time constant of the primary filter 348*d* may be adjusted. In this case, a desired time constant may be accepted by an input (not shown), for example.

Figure 26:
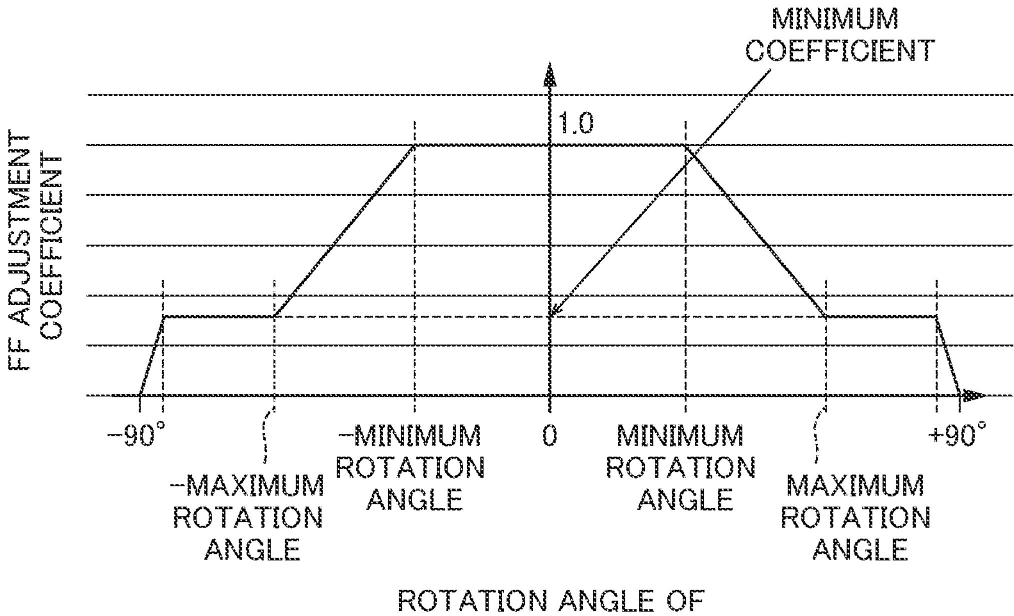
FIG. 26 is a diagram illustrating a relationship between a rotation angle of a link part 112*b* and an FF adjustment coefficient.

The second multiplier 348*e* multiplies the rotational angular speed vf26 provided through the primary filter 348*d* by an FF adjustment coefficient. FIG. 26 is a graph illustrating a relationship between the rotation angle of the link part 112*b* and the FF adjustment coefficient. The FF adjustment coefficient is a second adjustment coefficient for adjusting a value provided from the speed feed-forward control to the position feedback control loop. In FIG. 26, a horizontal axis indicates the rotation angle of the link part 112*b*, and a vertical axis indicates the FF adjustment coefficient.

As shown in FIG. 26, in the rotation of the link part 112*b*, the minimum rotation angle, the maximum rotation angle and +90 degrees are defined in a clockwise direction, and—the minimum rotation angle, the maximum rotation angle and −90 degrees are defined in a counterclockwise direction with respect to the second reference rotational position, which is defined 0 degree, and—the minimum rotation angle. The FF adjustment coefficient is a value ranging from 0 to 1.0. The FF adjustment coefficient is set to a value 1.0 until the link part 112*b* rotates to the minimum rotation angle in the clockwise direction. The FF adjustment coefficient linearly decreases to the minimum coefficient with rotation of the link part 112*b* from the minimum rotation angle to the maximum rotation angle. The minimum coefficient is 0.33, for example. The FF adjustment coefficient is a value corresponding to the minimum coefficient in rotation of the link part 112*b* from the maximum rotation angle to an angle close to +90 degrees. The FF adjustment coefficient linearly decreases to the minimum coefficient with rotation of the link part 112*b* to +90 degrees in a range close to +90 degrees. Also, the FF adjustment coefficient is set to a value 1.0 until the link part 112*b* rotates to the minimum rotation angle in the counterclockwise direction. The FF adjustment coefficient linearly decreases to the minimum coefficient with rotation of the link part 112*b* from—the minimum rotation angle to—the maximum rotation angle. The FF adjustment coefficient is a value corresponding to—the minimum coefficient in rotation of the link part 112*b* from—the maximum rotation angle to an angle close to −90 degrees. The FF adjustment coefficient linearly decreases to the minimum coefficient with rotation of the link part 112*b* to −90 degrees in a range close to −90 degrees. Because the link part 112*a* rotates in a direction opposite to a direction in which interference with the link part 112*c* is avoided if the absolute value of the rotation angle of the link part 112*b* becomes 90 degrees or more, the FF adjustment coefficient is set to zero when the absolute value of the rotation angle of the link part 112*b* is 90 degrees or more. The minimum coefficient, the minimum rotation angle, and the maximum rotation angle are parameters, and can be entered by using the touch panel 130, etc. The change of the FF adjustment coefficient in FIG. 26 is illustratively shown, and the change of the FF adjustment coefficient in accordance with the rotational position of the link part 112*b* is not limited to this. The FF adjustment coefficient is only required to monotonically increase from zero and then monotonically decrease to zero in accordance with change of the rotational position of the link part 112*b* from −90 degrees to +90 degrees.

As shown in FIG. 24, the rotation angle AG25 of the link part 112*b* detected by the encoder EN7*e* of the joint JT25 is provided to the second multiplier 348*e*. The first multiplier 348*c* determines the FF adjustment coefficient based on the provided rotation angle AG25, and multiplies the rotational angular speed vf26 provided through the primary filter 348*d* by the determined FF adjustment coefficient.

In a case in which the rotation angle of the link part 112*b* is increased from the first reference rotational position by operating of the grip part 112*d*, the rotation amount of the link part 112*a* about the A24 axis is increased by rotation of the link part 112*c* from the second reference rotational position. In this case, if a rotation speed of the link part 112*a* is high, the operator feels wrongness in the operation. The following description describe the wrongness.

Figure 27:
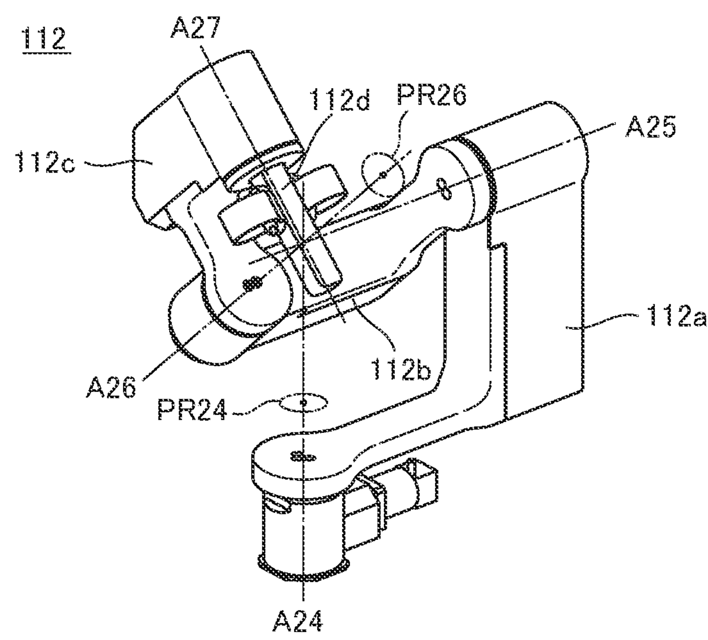
FIG. 27 is a diagram showing the wrist part with the link part 112*c* being rotated +45 degree from a first reference rotational position.
Figure 28:
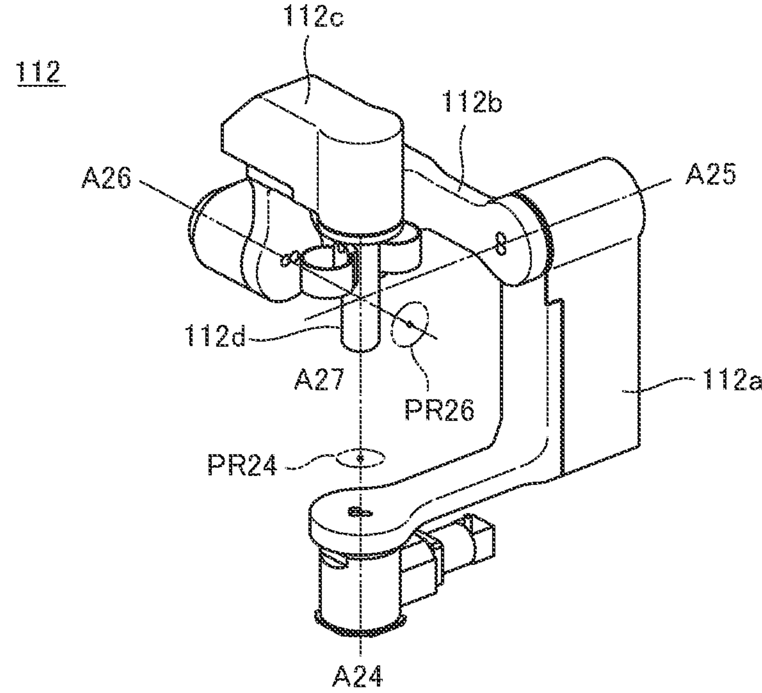
FIG. 28 is a diagram showing the wrist part with the link part 112*c* being rotated +90 degree from the first reference rotational position.

FIG. 27 is a diagram showing the wrist part 112 with the link part 112*b* being rotated +45 degree from the first reference rotational position. FIG. 28 is a diagram showing the wrist part 112 with the link part 112*b* being rotated +90 degree from the first reference rotational position. In FIGS. 27 and 28, a reference sign PR26 indicates a plane parallel to a rotational plane of the link part 112*c*, and a reference sign PR24 indicates a plane parallel to a rotational plane of the link part 112*a*.

As shown in FIG. 12, in the reference posture of the wrist part 112, the link part 112*b* is first positioned at the first reference rotational position. In this posture, the axis A26, which is a rotation axis of the link part 112*c*, agrees with the axis A24, which is a rotation axis of the link part 112*a*. Accordingly, if the link part 112*c* is rotated by a rotation angle θ from the second reference rotational position in accordance with operation on the grip part 112*d*, the link part 112*a* is rotated in the same direction as the link part 112*c* by the same angle as the rotation angle θ.

In a posture of the wrist part 112 shown in FIG. 27, the link part 112*b* is rotated +45 degrees from the first reference rotational position. In this posture, the axis A26 is inclined 45 degrees with respect to the A24 axis so that a plane parallel to the plane PR26, which is a rotation plane of the link part 112*c*, is inclined 45 degrees with respect to a plane parallel to the plane PR24, which is a rotation plane of the link part 112*a*. Accordingly, if the link part 112*c* is rotated by a rotation angle θ from the second reference rotational position in accordance with operation on the grip part 112*d*, the link part 112*a* is rotated by a rotation angle greater than the rotation angle θ in the plane parallel to the plane PR24, which is the rotation plane of the link part 112*a*.

In a posture of the wrist part 12 shown in FIG. 28, the link part 112*b* is rotated +90 degrees from the first reference rotational position. In this posture, the axis A26 is inclined 90 degrees with respect to the following rotation axis A4 so that a plane parallel to the plane PR26, which is the rotation plane of the link part 112*c*, is inclined 90 degrees with respect to the plane parallel to the plane PR24, which is the rotation plane of the link part 112*a*. Accordingly, in a case in which the link part 112*c* is rotated by a rotation angle θ from the second reference rotational position in accordance with operation on the grip part 112*d*, the link part 112*a* is rotated by a rotation angle substantially greater than the rotation angle θ in the plane parallel to the plane PR24, which is the rotation plane of the link part 112*a*.

In this case, if a rotation speed of the link part 112*a* is high, the operator feels wrongness in the operation.

To address this, as shown in FIG. 24, if the rotation angle of the link part 112*b* from the first reference rotational position is increased in accordance with operation on the grip part 112*d*, the second multiplier 348*e* can reduce the rotational angular speed of the link part 112*a* about the A24 axis, and as a result it is possible to prevent that the operator feels wrongness in the operation.

The reduction ratio corrector 348*f* converts the rotational angular speed vf26 that is multiplied by the FF adjustment coefficient into a rotational angular speed corresponding to a reduction ratio of the joint JT24 in reduction ratio correction. This reduction ratio correction is similar to a case of the reduction ratio corrector 341*b* described above.

The third multiplier, 348*g* is configured to generate a speed instruction v2 for feed-forward by multiplying the converted rotation angle by a predetermined.

In this embodiment, as described above, the operation controller 340 is configured to execute the following control based on a deviation between the second reference rotation position and a current rotation position of the link part 112*c*, and a rotation speed of the link part 112*c*. The operation controller 340 is configured to maintain the rotation amount of the link part 112*a* based on the rotation speed of the link part 112*c* and to reduce the rotation amount of the link part 112*a* based on the deviation if the absolute value of the moving speed of the gimbal point GP of the operation unit 110 is smaller than the predetermined thresholds. In other words, the position controller 341 is configured to calculate a deviation of the rotation angle AG26 from the second reference rotational position and to convert the deviation into a speed instruction v1. As discussed above, if the absolute value of the moving speed of the gimbal point GP of the operation unit 110 is smaller than the predetermined thresholds, the speed instruction v1 is multiplied by a predetermined coefficient smaller than 1. In other words, if the absolute value of the moving speed of the gimbal point GP of the operation unit 110 is smaller than the predetermined thresholds, the speed instruction v1 is reduced. The FF speed instruction generator 348 is configured to generate the speed instruction v2 based on the rotation speed of the link part 112*c*. Dissimilar to the speed instruction v1, the speed instruction v2 is not multiplied by a predetermined coefficient smaller than 1. Accordingly, the rotation amount of the link part 112*a* based on the rotation speed of the link part 112*c* is maintained even if the absolute value of the moving speed of the gimbal point GP of the operation unit 110 is smaller than the predetermined thresholds.

(Remote-Control-Apparatus Control Method)

Figure 29:
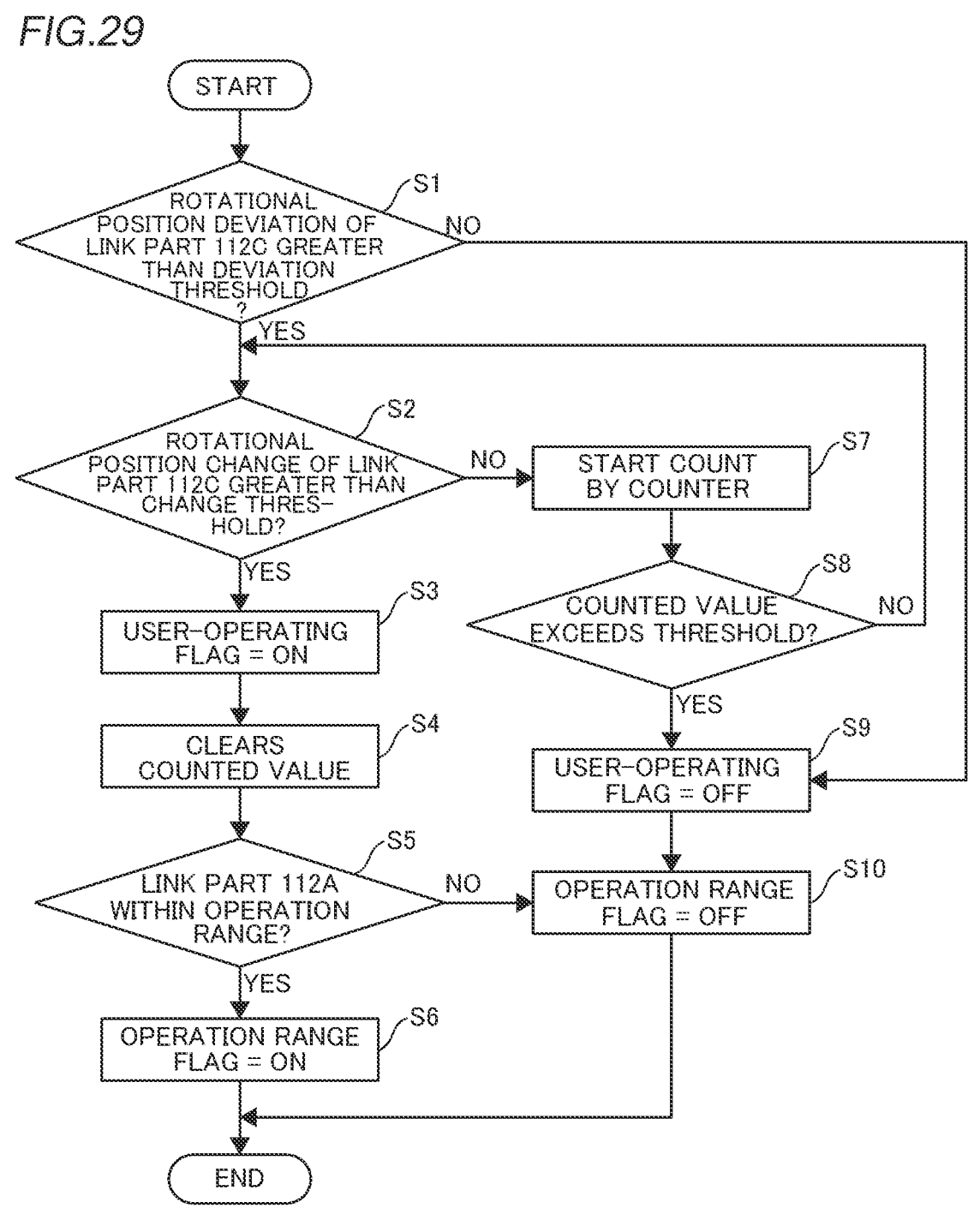

As shown in FIG. 29, in step S1, the operation controller 340 determines whether a rotational position deviation of the link part 112*c* is greater than a rotation deviation threshold. For example, the rotational deviation threshold is 1.0 degree. Depending on a result of this step S1, the dead band part 341*d* of the position controller 341 is activated.

If No in step S1, the user-operating flag f1 and the operation range flag f2 are brought in OFF in steps S9 and S10. In addition, the first switch 341*e*, the second switch 341*f*, and the third switch 348*b* of the FF speed instruction generator 348 of the position controller 341 are brought in OFF.

If Yes in step S1, the operation controller 340 determines whether a rotational position change of the link part 112*c* is greater than a change threshold in step S2. The rotational position change is a difference between a current rotational position and a previous rotational position of the link part 112*c*.

If No in step S2, the operation controller 340 starts count by using a counter in step S7. Subsequently, the operation controller 340 determines whether a counted value exceeds a threshold in step S8. For example, the threshold is 1000 ms. This count is stopped when the rotational position change of the link part 112*c* exceeds the change threshold. If No in step S8, the operation controller 340 determines that the operation unit 110 is operated, and returns to step S2.

If Yes in step S8, that is, if no operation is made for 1000 ms or more, the operation controller 340 determines that the operation on the operation unit 110 is stopped, and turns the user-operating flag f1 and the operation range flag f2 OFF in steps S9 and S10.

If Yes in step S2, the operation controller 340 determines that the operation unit 110 is being operated, and brings the user-operating flag f1 into OFF in step S3 and clears the counted value of the counter in step S4. Accordingly, the first switch 341*e* of the position controller 341 is turned ON.

The operation controller 340 determines whether the link part 112*a* is within the operation range in step S5. If No in step S5, the operation range flag f2 is turned OFF in step S10.

If Yes in step S5, the operation controller 340 turns the operation range flag f2 ON in step S6.

As a result, the second switch 341*f* of the position controller 341 and the third switch 348*b* of the FF speed instruction generator 348 are turned on, and position feedback control and feed-forward control are performed. In other words, the operation controller 340 is configured to execute following control in which the link part 112*a* is rotated about the A24 axis based on a rotational position of the link part 112*c* by the servomotor SM7*d* to keep an angle formed by the link part 112*c* and the link part 112*b* at a predetermined angle. In this embodiment, a rotation amount of the link part 112*a* about the A24 axis in the following control in a case in which an absolute value of a moving speed of a gimbal point GP of the operation unit 110 is smaller than predetermined thresholds is smaller than in a case in which the absolute value is not smaller than the predetermined thresholds. That is, as described above, the operation controller 340 is configured to execute the following control based on a value obtained by multiplying the speed instruction v1 based on a deviation between the second reference rotational position and the current rotational position of the link part 112_c_ by a predetermined coefficient. In a case in which the following control is executed, even when the link part 112_c_ is rotated toward the link part 112_b_ by an operator, rotation of link part 112_a_ moves the link part 112_b_ away from the link part 112_c_ so that the link part 112_c_ and link part 112_b_ form a right angle, and as a result it is possible to prevent interference between the link part 112_c_ and the link part 112_b_.

Experiment

Figure 30:
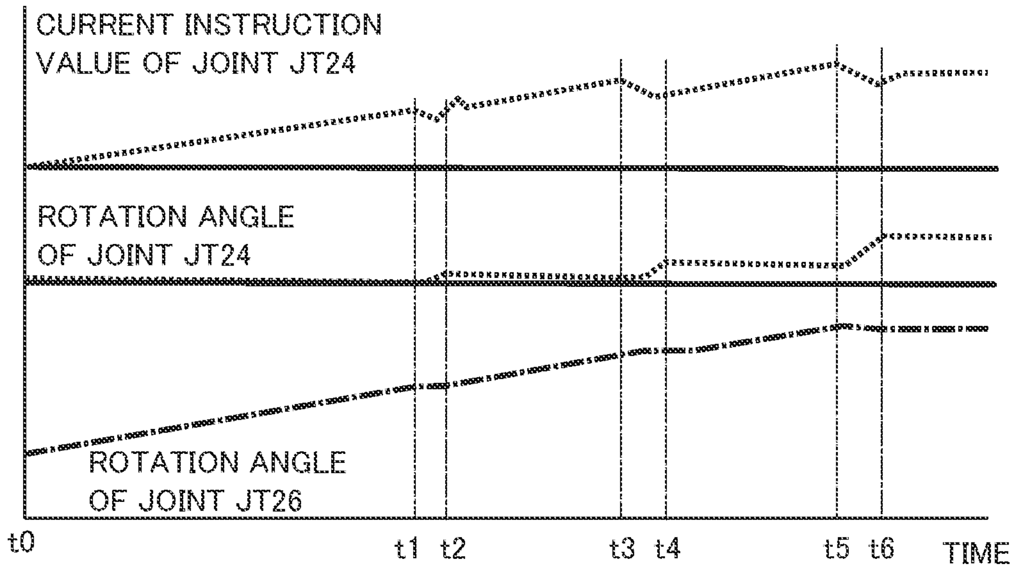
FIG. 30 is a diagram illustrating an experimental result of the following control.

Solid lines in FIG. 30 indicate a rotation angle and a current instruction value of the joint JT24 in the configuration according to this disclosure in which a rotation amount of the link part 112_a_ about the A24 axis is reduced in accordance with a moving speed of the gimbal point GP of the operation unit 110. Dotted lines in FIG. 30 indicate a rotation angle and a current instruction value of the joint JT24 in a configuration of a comparative example in which a rotation amount of the link part 112_a_ about the A24 axis is not reduced in accordance with a moving speed of the gimbal point GP of the operation unit 110. Alternate long and short dashed lines in FIG. 30 indicates a rotation angle of the joint JT26. In FIG. 30, the rotation angle of the joint JT26 gradually increases from time t0 to time t1. In the comparative example, the current instruction value of the servo motor SM7_d_, which is configured to rotate the joint JT24, is gradually increased from time t0 to time t1 by following control of the comparative example. However, because friction is produced in the joint JT24, the rotation angle of the joint JT24 is roughly fixed from time t0 to time t1. After that, the joint JT24 rotates between time t1 and time t2. From this result, it was confirmed that the surgical instrument 1 could not follow an operation of an operator on the operation unit 110 between time t1 and time t2. Also, it was confirmed that the surgical instrument 1 could not follow the operation of the operator on the operation unit 110 between time t3 and time t4, and between time t5 and time t5 where the joint JT24 rotates.

Contrary to this, as shown by the solid lines in FIG. 30, in the configuration according to this disclosure, between time t1 and time t6 where an absolute value of the moving speed of the gimbal point GP of the operation unit 110 is small, although the rotation angle of joint JT26 is increased, the rotation amount of the link part 112_a_ about the A24 axis is zero. Consequently, it was confirmed that the surgical instrument 1 could follow the operation of the operator on the operation unit 110.

Advantages of the Embodiment

A rotation amount of the link part 112_a_ about the A24 axis in the following control in a case in which an absolute value of a moving speed of a gimbal point GP of the operation unit 110 is smaller than predetermined thresholds is smaller than in a case in which the absolute value is not smaller than the predetermined thresholds. Accordingly, when an absolute value of a moving speed of the gimbal point GP of the operation unit 110 by operation of an operator is smaller than predetermined thresholds, for example, when the absolute value is relatively slow, a rotation amount of the link part 112_a_ about the A24 axis is small. As a result, even in a case in which a moving speed of the gimbal point GP of the operation unit 110 gradually increases, even when the link part 112_a_ starts to rotate, the rotation amount of the link part 112_a_ is small. In other words, it is possible to prevent that the link part 112_a_ that cannot rotate to follow a rotation of the link part 112_c_ and is stationary starts to rapidly rotate. Therefore, the surgical instrument 1 can be smoothly moved to follow an operation on the operation unit 110 by the operator even when the gimbal point GP of the operation unit 110 relatively slowly moves.

The operation controller 340 is configured to set the rotation amount of the link part 112_a_ to zero in the following control if the absolute value of the moving speed of the gimbal point GP of the operation unit 110 is smaller than the first threshold Th1. Accordingly, if the absolute value of the moving speed of the gimbal point GP of the operation unit 110 is smaller than the first threshold Th1, because the following control of the link part 112_a_ is not executed, it is possible to reliably prevent that the link part 112_a_ start to rapidly rotate, and that the surgical instrument 1 cannot smoothly move to follow the operation on the operation unit 110 by the operator.

The predetermined thresholds include the first threshold Th1, and the second threshold Th2 whose absolute value is greater than the first threshold Th1; and the operation controller 340 is configured to set the rotation amount of the link part 112_a_ to zero in the following control if the absolute value of the moving speed of the gimbal point GP of the operation unit 110 is smaller than the first threshold Th1, to increase the rotation amount of the link part 112_a_ in the following control from zero to a predetermined rotation amount with increase of the moving speed of the gimbal point GP of the operation unit 110 if the absolute value of the moving speed of the gimbal point GP of the operation unit 110 is not smaller than the first threshold Th1 and smaller than the second threshold Th2, and to set the rotation amount of the link part 112_a_ to the predetermined rotation amount in the following control if the absolute value of the moving speed of the gimbal point GP of the operation unit 110 is not smaller than the second threshold Th2. Accordingly, because the rotation amount of the link part 112_a_ is prevented from rapidly changing from zero to the predetermined rotation amount, it is possible to prevent the rotation amount of the link part 112_a_ from rapidly changing.

The operation controller 340 is configured to execute the following control based on a deviation between a reference rotation position and a current rotation position of the link part 112_c_, and a rotation speed of the link part 112_c_, and to maintain the rotation amount of the link part 112_a_ based on the rotation speed of the link part 112_c_ and to reduce the rotation amount of the link part 112_a_ based on the deviation if the absolute value of the moving speed of the gimbal point GP of the operation unit 110 is smaller than the predetermined thresholds. In a case in which the moving speed of the gimbal point GP of the operation unit 110 is slow, the deviation between the reference rotational position and the current rotational position of the link part 112_c_ becomes dominant in the following control. For this reason, if the absolute value of the moving speed of the gimbal point GP of the operation unit 110 is smaller than the predetermined thresholds, the rotation amount of the link part 112_a_ can be effectively reduced by reducing the rotation amount of the link part 112_a_ based on the deviation.

The operation controller 340 is configured to execute the following control based on a value obtained by multiplying the speed instruction based on the deviation between the reference rotational position and the current rotational position of the link part 112_c_ by a predetermined coefficient, and the predetermined coefficient in a case in which the absolute value of the moving speed of the gimbal point GP of the operation unit 110 is smaller than the predetermined threshold is smaller than in a case in which the absolute value is not smaller than the predetermined threshold. Consequently, the operation controller 340 can easily change the rotation amount of the link part 112*a* by simply changing the coefficient.

Modified Embodiment

Note that the embodiment disclosed this time must be considered as illustrative in all points and not restrictive. The scope of the present invention is not shown by the above description of the embodiments but by the scope of claims for patent, and all modifications or modified examples within the meaning and scope equivalent to the scope of claims for patent are further included.

While the example in which the rotation amount of the link part 112*a* is set to zero in the following control if the absolute value of the moving speed of the gimbal point GP of the operation unit 110 is smaller than the first threshold Th1 has been shown in the aforementioned embodiment, the present disclosure is not limited to this. For example, if the absolute value of the moving speed of the gimbal point GP of the operation unit 110 is smaller than the first threshold Th1, the rotation amount of the link part 112*a* may be to set a value greater than zero and close to zero in the following control.

While the example in which the rotation amount of the link part 112*a* in the following control is linearly increased from zero to a predetermined rotation amount with increase of the moving speed of the gimbal point GP of the operation unit 110 if the absolute value of the moving speed of the gimbal point GP of the operation unit 110 is not smaller than the first threshold Th1 and smaller than the second threshold Th2 has been shown in the aforementioned embodiment, the present disclosure is not limited to this. For example, the rotation amount of the link part 112*a* in the following control may be increased quadratically, exponentially or in another form other than the linear form with increase of the moving speed of the gimbal point GP of the operation unit 110.

While the example in which the rotation amount of the following link part based on the rotation speed is maintained by the FF speed instruction generator 348, and the rotation amount of the link part 112*a* based on the deviation is reduced by the position controller 341 if the absolute value of the moving speed of the gimbal point GP of the operation unit 110 is smaller than the predetermined thresholds has been shown in the aforementioned embodiment, the present disclosure is not limited to this. For example, the rotation amount of the following link part based on the rotation speed may be reduced by the FF speed instruction generator 348 if the absolute value of the moving speed of the gimbal point GP of the operation unit 110 is smaller than the predetermined thresholds.

While the example in which four robot arms 50 are provided has been shown in the aforementioned embodiment, the present disclosure is not limited to this. In the present disclosure, any number of robot arms 50 may be provided as long as at least one robot arms are provided.

While the example in which the arms 51 and the positioner 30 are constructed of a 7-axis multi-joint robot has been shown in the aforementioned embodiment, the present disclosure is not limited to this. For example, the arms 51 and the positioner 30 are constructed of a multi-joint robot having an axis configuration other than the 7-axis multi-joint robot. The multi-joint robot having an axis configuration other than the 7-axis multi-joint robot can be a 6-axis or 8-axis multi-joint robot, for example.

While the example in which the surgical robot 100 includes the medical cart 10, the positioner 30 and the arm base 40 has been shown in the aforementioned embodiment, the present disclosure is not limited to this. The medical cart 10, the positioner 30 and the arm base 40 are not necessarily provided, and the surgical robot 100 may include only the robot arms 50, for example.

Functions of elements disclosed in this specification can be realized by a circuit or processing circuit including a general purpose processor, a dedicated processor, an Integrated circuit, ASIC (Application Specific Integrated Circuits), a conventional circuit and/or combination of them configured or programmed to realize the functions disclosed. Because processors include transistors and other circuits, they are considered as a processing circuit or a circuit. In the present disclosure, circuits, units or means are hardware for realizing the functions stated above, or hardware programmed to realize the functions stated above. The hardware can be hardware disclosed in this specification, or may be other known hardware programed or configured to realize the functions stated above. In the case in which the hardware is a processor that can be considered as one type of circuits, the circuit, means or unit is a combination of hardware and software, and the software is used for configuration of the hardware and/or the processor.

What is claimed is:

1. An operation device comprising:

an operation unit configured to accept an operation on a surgical instrument attached to a distal end of a robot arm; and a controller, wherein the operation unit includes an arm part and a wrist part, the wrist part includes a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the controller is configured to perform operations comprising operations to:

execute following control in which the following link part is rotated about the following rotation axis based on a rotational position of the second link part by the driver to keep an angle formed by the second link part and the first link part at a predetermined angle, a rotation amount of the following link part about the following rotation axis in the following control in a case in which an absolute value of a moving speed of the wrist part by the operation of the operator is smaller than a plurality of predetermined thresholds, is smaller than in a case in which the absolute value is not smaller than the plurality of predetermined thresholds;

the plurality of predetermined thresholds include a first threshold, and a second threshold whose absolute value is greater than the first threshold; and the controller is configured to perform operations further comprising operations to:

set the rotation amount of the following link part to zero in the following control if the absolute value of the moving speed of the wrist part by the operation of the operator is smaller than the first threshold, increase the rotation amount of the following link part according to a coefficient from zero to a predetermined rotation amount, the coefficient determined based on an increase of a rotation speed of the second link part in the following control if the absolute value of the moving speed of the wrist part by the operation of the operator is not smaller than the first threshold and smaller than the second threshold, and set the rotation amount of the following link part to the predetermined rotation amount in the following control if the absolute value of the moving speed of the wrist part by the operation of the operator is not smaller than the second threshold.

2. The operation device according to claim 1, wherein the controller is configured to linearly, quadratically or exponentially increase the rotation amount of the following link part from zero to the predetermined rotation amount with increase of the rotation speed of the second link part in the following control if the absolute value of the moving speed of the wrist part by the operation of the operator is not smaller than the first threshold and smaller than the second threshold.

3. The operation device according to claim 1, wherein the first threshold is not smaller than 20 mm/s and not greater than 30 mm/s; and the second threshold is not smaller than 100 mm/s and not greater than 150 mm/s.

4. The operation device according to claim 1, wherein the controller is configured perform operations further comprising operations to execute the following control based on a deviation between a reference rotational position and a current rotational position of the second link part, and a rotation speed of the second link part, and to maintain the rotation amount of the following link part based on the rotation speed and to reduce the rotation amount of the following link part based on the deviation if the absolute value of the moving speed of the wrist part by the operation of the operator is smaller than the plurality of predetermined thresholds.

5. The operation device according to claim 1, wherein the controller is configured to perform operations further comprising operations to execute the following control based on a value obtained by multiplying a speed instruction based on a deviation between a reference rotational position and a current rotational position of the second link part by a predetermined coefficient; and the predetermined coefficient in a case in which the absolute value of the moving speed of the wrist part by the operation of the operator is smaller than the predetermined threshold is smaller than in a case in which the absolute value of the moving speed of the wrist part by the operation of the operator is not smaller than the plurality of predetermined thresholds.

6. The operation device according to claim 1, wherein the moving speed of the wrist part is a moving speed of a gimbal point, which is an intersection of the plurality of rotation axes of the operation unit.

7. The operation device according to claim 1, further comprising a second operation unit configured to accept an operation on a second surgical instrument attached to a distal end of a second robot arm, wherein the second operation unit includes a second arm part and a second wrist part, the second wrist part includes a second following link part including a proximal end connected to a distal end of the second arm part, and configured to rotate about a second following rotation axis, a third link part including a proximal end connected to a distal end of the second following link part, and configured to rotate about a fourth rotation axis, a fourth link part including a proximal end connected to a distal end of the third link part, and configured to rotate about a fifth rotation axis orthogonal to the fourth rotation axis, a second grip part including a second grip member configured to be grasped by the operator and a proximal end connected to a distal end of the fourth link part, and configured to rotate about the sixth rotation axis orthogonal to the fifth rotation axis and the fourth rotation axis, and a second driver configured to rotate the second following link part about the second following rotation axis, the controller is configured to perform operations comprising operations to execute second following control in which the second following link part is rotated about the second following rotation axis based on a rotational position of the fourth link part by the second driver to keep an angle formed by the fourth link part and the third link part at a predetermined angle, and a rotation amount of the second following link part about the second following rotation axis in the second following control in a case in which an absolute value of a moving speed of the second wrist part by the operation of the operator is smaller than the plurality of predetermined thresholds is smaller than in a case in which the absolute value is not smaller than the plurality of predetermined thresholds.

8. A robotic surgical system comprising:

a surgical device including a robot arm including a distal end to which a surgical instrument is attached;

an operation device including an operation unit configured to accept an operation on the surgical instrument; and a controller, wherein the operation unit includes an arm part and a wrist part, the wrist part, includes a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the controller is configured to perform operations comprising operations to execute following control in which the following link part is rotated about the following rotation axis based on a rotational position of the second link part by the driver to keep an angle formed by the second link part and the first link part at a predetermined angle, a rotation amount of the following link part about the following rotation axis in the following control in a case in which an absolute value of a moving speed of the wrist part by the operation of the operator is smaller than a plurality of predetermined thresholds is smaller than in a case in which the absolute value is not smaller than the plurality of predetermined thresholds, the plurality of predetermined thresholds include a first threshold, and a second threshold whose absolute value is greater than the first threshold; and the controller is configured to perform operations further comprising operations to:

set the rotation amount of the following link part to zero in the following control if the absolute value of the moving speed of the wrist part by the operation of the operator is smaller than the first threshold, increase the rotation amount of the following link part according to a coefficient from zero to a predetermined rotation amount, the coefficient determined based on an increase of a rotation speed of the second link part in the following control if the absolute value of the moving speed of the wrist part by the operation of the operator is not smaller than the first threshold and smaller than the second threshold, and set the rotation amount of the following link part to the predetermined rotation amount in the following control if the absolute value of the moving speed of the wrist part by the operation of the operator is not smaller than the second threshold.

9. The robotic surgical system according to claim 8, wherein the controller is configured to execute the following control based on a deviation between a reference rotational position and a current rotational position of the second link part, and a rotation speed of the second link part, and to maintain the rotation amount of the following link part based on the rotation speed and to reduce the rotation amount of the following link part based on the deviation if the absolute value of the moving speed of the wrist part by the operation of the operator is smaller than the plurality of predetermined thresholds.

10. The robotic surgical system according to claim 8, wherein the controller is configured to execute the following control based on a value obtained by multiplying a speed instruction based on a deviation between a reference rotational position and a current rotational position of the second link part by a predetermined coefficient; and the predetermined coefficient in a case in which the absolute value of the moving speed of the wrist part by the operation of the operator is smaller than the plurality of predetermined thresholds is smaller than in a case in which the absolute value of the moving speed of the wrist part by the operation of the operator is not smaller than the plurality of predetermined thresholds.

11. An operation-device control method of an operation device including an operation unit configured to accept an operation on a surgical instrument attached to a distal end of a robot arm, and a controller, the operation unit including an arm part and a wrist part, the wrist part including a following link part including a proximal end connected to a distal end of the arm part, and configured to rotate about a following rotation axis, a first link part including a proximal end connected to a distal end of the following link part, and configured to rotate about a first rotation axis, a second link part including a proximal end connected to a distal end of the first link part, and configured to rotate about a second rotation axis orthogonal to the first rotation axis, a grip part including a grip member configured to be grasped by an operator and a proximal end connected to a distal end of the second link part, and configured to rotate about a third rotation axis orthogonal to the second rotation axis and the first rotation axis, and a driver configured to rotate the following link part about the following rotation axis, the method comprising:

acquiring a rotational position of the second link part; and executing following control in which the following link part is rotated about the following rotation axis based on the rotational position of the second link part by the driver to keep an angle formed by the second link part and the first link part at a predetermined angle, wherein a rotation amount of the following link part about the following rotation axis in the following control in a case in which an absolute value of a moving speed of the wrist part by the operation for operating the surgical instrument is smaller than a plurality of predetermined thresholds is smaller than in a case in which the absolute value is not smaller than the plurality of predetermined thresholds the plurality of predetermined thresholds include a first threshold, and a second threshold whose absolute value is greater than the first threshold;

the rotation amount of the following link part is set to zero in the following control if the absolute value of the moving speed of the wrist part by the operation of the operator is smaller than the first threshold, the rotation amount of the following link part is increased according to a coefficient from zero to a predetermined rotation amount, the coefficient determined based on an increase of a rotation speed of the second link part in the following control if the absolute value of the moving speed of the wrist part by the operation of the operator is not smaller than the first threshold and smaller than the second threshold, and the rotation amount of the following link part is set to the predetermined rotation amount in the following control if the absolute value of the moving speed of the wrist part by the operation of the operator is not smaller than the second threshold.

12. The operation-device control method according to claim 11, wherein the controller is configured to perform operations comprising operations to execute the following control based on a deviation between a reference rotational position and a current rotational position of the second link part, and a rotation speed of the second link part, and to maintain the rotation amount of the following link part based on the rotation speed and to reduce the rotation amount of the following link part based on the deviation if the absolute value of the moving speed is smaller than the plurality of predetermined thresholds.

13. The operation-device control method according to claim 11, wherein the controller is configured to perform operations comprising operations to execute the following control based on a value obtained by multiplying a speed instruction based on a deviation between a reference rotational position and a current rotational position of the second link part by a predetermined coefficient; and the predetermined coefficient in a case in which the absolute value of the moving speed is smaller than the plurality of predetermined thresholds is smaller than in a case in which the absolute value of the moving speed is not smaller than the plurality of predetermined thresholds.

14. The operation-device control method according to claim 11, wherein the moving speed of the wrist part is a moving speed of a gimbal point, which is an intersection of the plurality of rotation axes of the operation unit.

* * * * *